US009790487B2

(12) United States Patent
Babb et al.

(10) Patent No.: US 9,790,487 B2
(45) Date of Patent: *Oct. 17, 2017

(54) RAPID ASSEMBLY OF MULTIPLE ARBITRARY LENGTH DNA FRAGMENTS

(71) Applicant: Massachusetts Institute of Technology, Cambridge, MA (US)

(72) Inventors: Jonathan William Babb, Watertown, MA (US); Shuo Cory Li, Cambridge, MA (US); Thomas Knight, Cambridge, MA (US); Ron Weiss, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/272,159

(22) Filed: Sep. 21, 2016

(65) Prior Publication Data

US 2017/0130220 A1    May 11, 2017

Related U.S. Application Data

(63) Continuation of application No. 13/825,684, filed as application No. PCT/US2011/053088 on Sep. 23, 2011, now Pat. No. 9,487,808.

(60) Provisional application No. 61/454,481, filed on Mar. 18, 2011, provisional application No. 61/386,401, filed on Sep. 24, 2010.

(51) Int. Cl.
*C12P 19/34* (2006.01)
*C12N 15/10* (2006.01)

(52) U.S. Cl.
CPC ..... *C12N 15/1027* (2013.01); *C12N 15/1031* (2013.01); *C12P 19/34* (2013.01)

(58) Field of Classification Search
None
See application file for complete search history.

(56) References Cited

U.S. PATENT DOCUMENTS 6,537,776 B1    3/2003   Short
9,487,808 B2 * 11/2016   Babb .................. C12N 15/1027
2006/0029935 A1 2/2006   Carrino et al.
2009/0123973 A1 5/2009   Reed

FOREIGN PATENT DOCUMENTS

WO       WO 98/38297 A1    9/1998

OTHER PUBLICATIONS

Babb et al., Rapid multistep biobrick assembly using programmable magnetic bead-based solid phase probes. SynBERC. 2010.
Ellis et al., DNA assembly for synthetic biology: from parts to pathways and beyond. Integr Biol (Camb). Feb. 2011;3(2):109-18. doi: 10.1039/c0ib00070a. Epub Jan. 19, 2011.
Gibson, Synthesis of DNA fragments in yeast by one-step assembly of overlapping oligonucleotides. Nucleic Acids Res. Nov. 2009;37(20):6984-90. doi:10.1093/nar/gkp687.
Shetty et al., Engineering BioBrick vectors from BioBrick parts. J Biol Eng. Apr. 14, 2008;2:5. doi: 10.1186/1754-1611-2-5.

* cited by examiner

*Primary Examiner* — Jim Ketter
(74) *Attorney, Agent, or Firm* — Wolf, Greenfield & Sacks, P.C.

(57) ABSTRACT

Aspects herein relate to composition, and related methods, for isolating and assembling DNA molecules without intermediate cloning steps.

26 Claims, 20 Drawing Sheets

Successful conversion of BioBricks to self-assembling parts

Legend:
Lane 1. hyperladder 1

Overhang1_J85206_Overhang2:
Lane 2. Supernatant and wash 1
Lanes 3-5. wash 2-4
Lane 6. eluted part Overhang2_J85204_Overhang1:
Lane 7. Supernatant and wash 1
Lane 8-10. wash 2-4
Lane 11. eluted part

PCR Verification of overhang ligation

Legend:
Lane 1: 1ul hyperladder 1
Lane 2: Correct PCR product Overhang2_J85204_Overhang1

Figure 6

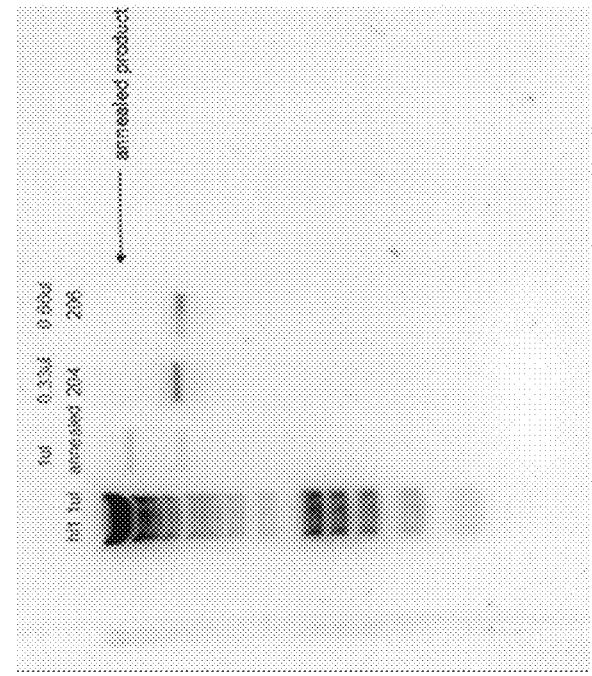

Figure 6: Electrophoresis result demonstrating successful self-assembly (via annealing) of two parts, one with a BioBrick backbone attached. Annealed in low salt (MgCl2) buffer with 5% PEG at 50C for 1 hour. Product is Ecorl_J85204_J85333:J85330_J85206-PSB1A2_Ecorl Legend:
Lane 1: 1ul hyperladder I
Lane 2: Annealed product (J85208. 6750bp including PSB1A2 backbone) (3ul)
Lane3: J85204 with J85333 overhang (6ul x 17ng/ul)
Lane 4: PSB1A2-J58206 with J85330 overhang (3ul x 38ng/ul)

Exo I cleanup characterization

Legend:
1. Hyperladder 5
2. single stranded DNA control (J85331)
3. no ssDNA (J85331) after ExoI digest
4. Hyperladder 1
5. I13522 cut with PstI (linear dsDNA control)
6. I13522 PstI, ExoI (dsDNA unaffected)

Open Plasmid with *EcoRI* or *PstI* cut

Chewback Choices

- T4 pol 3' -> 5' exonuclease (without dNTPs)
- T5 exo 5' → 3' exonuclease
  - One step / combined with polymerase fill-in
  - Separate step before fill-in Digest & chewback of BioBrick Part

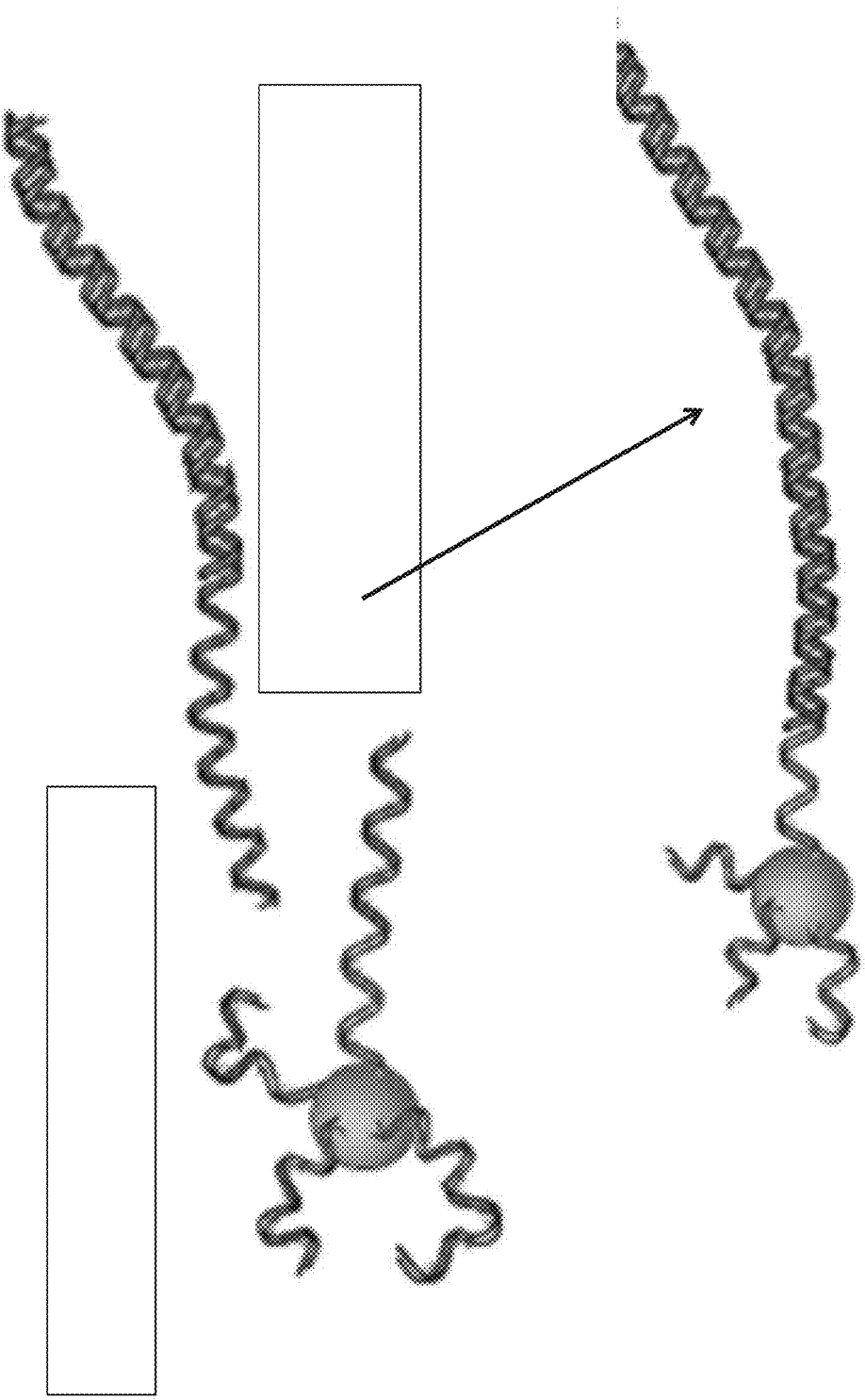

Figure 11
Example of Prefix Part on Anchor

- 1. Prefix part annealed to prefix anchor:

AATTCGGGCCGCTTCTAGANNNNNNNNN       NNNNNNN
  B–CAAAGAAUCTTAAGCGCCGGGCGAAGATCT

- 2. Prefix part annealed and ligated to anchor:

AATTCGGGCCGCTTCTAGANNNNNNNNNNNNNNNNN
  B–CAAAGAAUCTTAAGCGCCGGGCCGAAGATCTNNNNNNNNNN

- 3. Prefix part annealed, ligated, cut with SpeI:

AATTCGGGCCGCTTCTAGANNNNNNNN
  B–CAAAGAAUCTTAAGCGCCGGGCCGAAGATCTNNNNNNNNNGATC

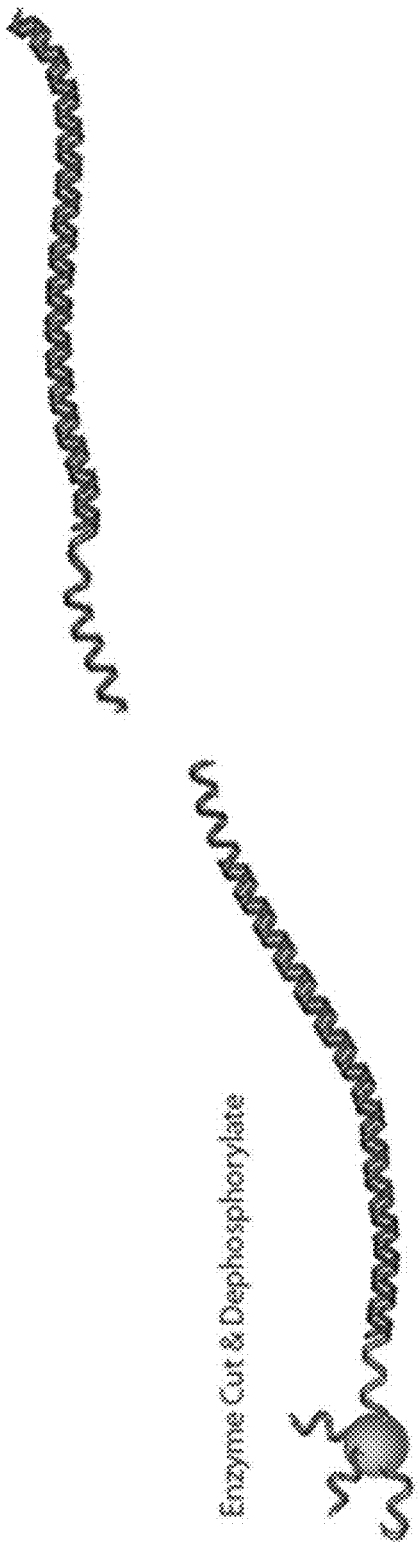

Probe part and remove backbone

Legend:
Lane 1. hyperladder I
Lane 2. supernatant of J10000 cut with EcorI chewed with T4 DNA polymerase probed with J85310
Lane 3. wash
Lane 4. cut with SpeI, supernatant
Lane 5. wash
Lane 6. elute part at 80C Multistep assembly in log(N) steps Binary Assembly Complete construction reduced from days to hours

Figure 16

Example purification of part from backbone using temporary overhang created on backbone rather than part.

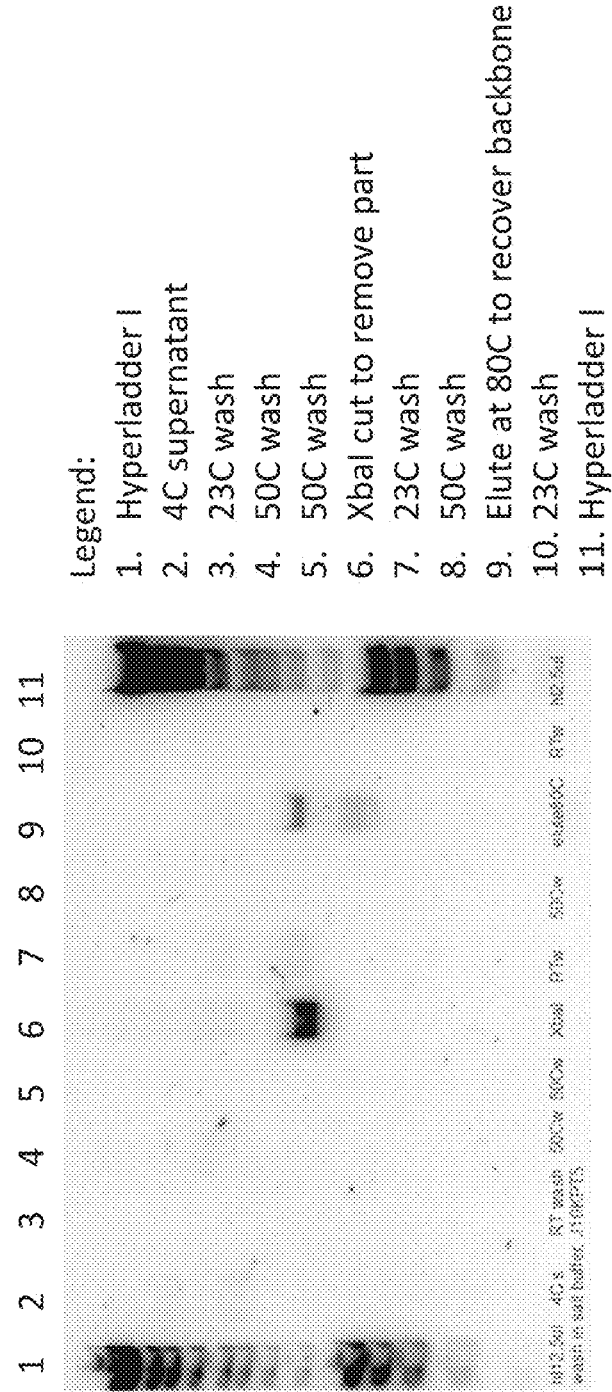

Legend:
1. Hyperladder I
2. 4C supernatant
3. 23C wash
4. 50C wash
5. 50C wash
6. XbaI cut to remove part
7. 23C wash
8. 50C wash
9. Elute at 80C to recover backbone
10. 23C wash
11. Hyperladder I BioBrick J10000, cut with PstI, 5' chewed with 1:100 T5 for 20 minutes at 37C, annealed to beaded J85325. Part is cleanly separate with XbaI cut. Backbone is still on anchor and elutes at 80C (note some is ssDNA in lower bands on gel lane 9 but will reanneal).

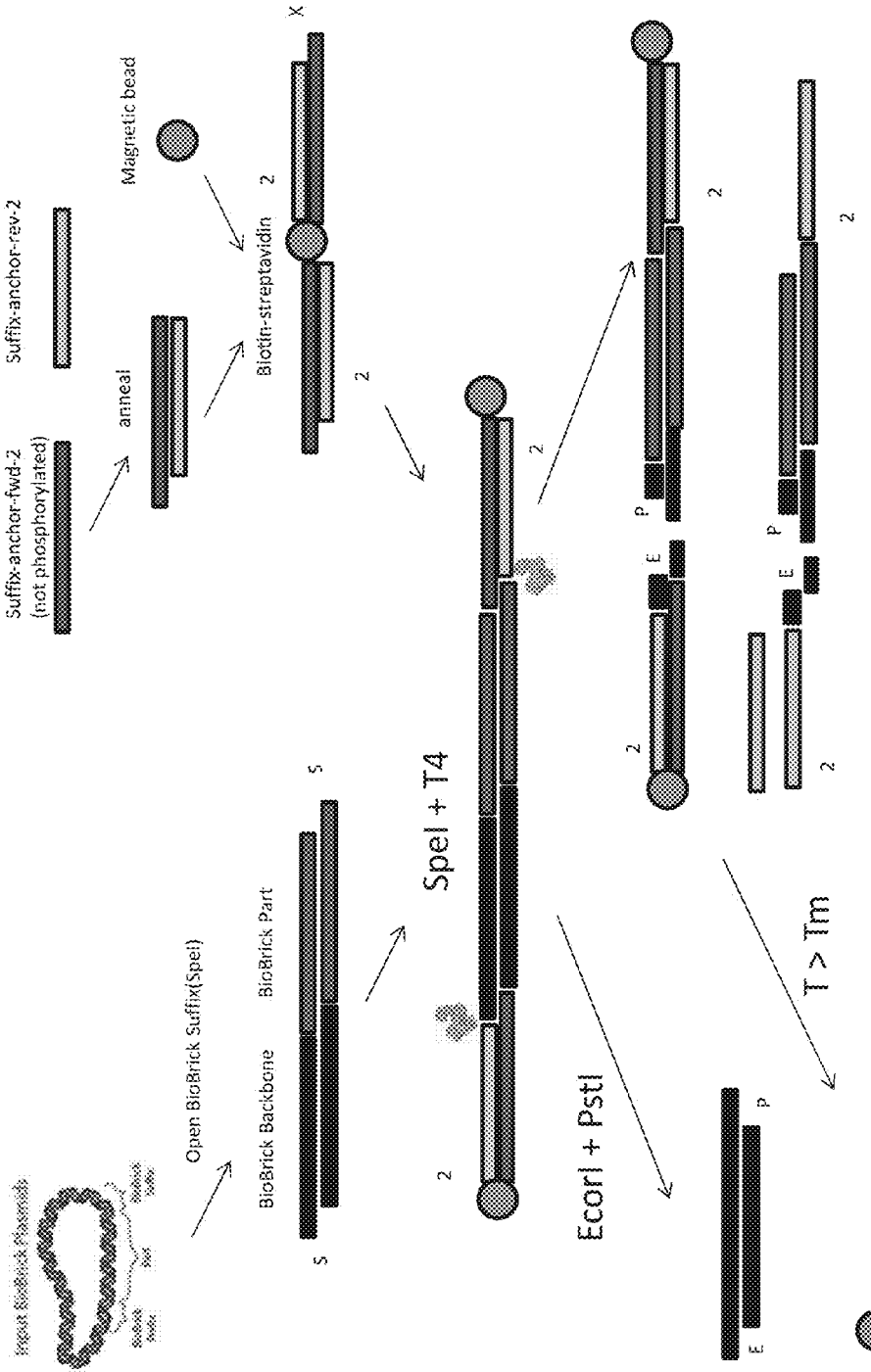

Adding Prefix / Purify Suffix

RAPID ASSEMBLY OF MULTIPLE ARBITRARY LENGTH DNA FRAGMENTS

RELATED APPLICATIONS

This application is a continuation of U.S. application Ser. No. 13/825,684, filed Oct. 25, 2013, which is a national stage filing under 35 U.S.C. §371 of international PCT application PCT/US2011/053088, filed Sep. 23, 2011, which was published under PCT Article 21(2) in English and which claims the benefit under 35 U.S.C. §119(e) of U.S. provisional application Ser. No. 61/454,481, filed Mar. 18, 2011, and of U.S. provisional application Ser. No. 61/386,401, filed Sep. 24, 2010, the disclosures of which are incorporated by reference herein in their entireties.

GOVERNMENT SUPPORT

This invention was made with government support under Grant No. EEC0540879 awarded by the National Science Foundation. The government has certain rights in the invention.

FIELD OF THE INVENTION

Aspects herein relate to compositions, and related methods, for isolating and assembling DNA molecules without intermediate cloning steps.

BACKGROUND OF THE INVENTION

A major advance in the field of synthetic biology is the concept of the standardized part, a unit of DNA that is flanked by standard prefix and suffix sequences that enable modular assembly of composite parts from basic parts. Parts may be stored and reused or shared between research labs. The wide variety of different composite parts that may be combinatorially constructed from basic parts and previously assembled composite parts enables a large and growing set of synthetic biology applications.

While a major advancement in the field, at the same time the assembly of DNA parts into larger DNA constructs is currently a limiting technology in the engineering of biological system (DNA assembly for synthetic biology: from parts to pathways and beyond, T. Ellis, et al., *Integr. Biol.*, 2011, 3, 109-118). Laborious recombinant cloning processes that take several days are required to combine just two DNA parts into a new construct. New biological systems composed of many genes may only be realized after weeks or months of cloning.

SUMMARY OF THE INVENTION

Aspects provided herein related to a DNA assembly method and related double probing technique for sequence-specific purification. The embodiments described herein address the above limitations by automatically converting a set of standard parts into self-assembling parts, which are an ordered set of molecules with uniquely encoded overhangs that combine in a specific order through annealing to self-assemble a larger DNA molecule. In certain embodiments, this conversion process may use standard restriction enzymes and ligase in combination with reusable paramagnetic beads and biotinylated oligonucleotides (oligos). In certain aspects, self-assembly into new DNA constructs is accomplished by mixing, heating the samples, and allowing to cool (annealing). Elimination of cloning, in some aspects, reduces assembly time from days to hours, minimizes the possibility of mutations, and supports intermediate constructs that may be toxic to the cell or otherwise render the cell difficult to grow. In some aspects, the methods described herein may be automated using liquid handling robots or microfluidic devices.

According to one aspect of the invention, methods of assembling a plurality of DNA molecules are provided. The methods include preparing a double-stranded (ds)DNA molecule containing (i) a first 5' overhang DNA sequence of at least 10 nucleotides on a first strand of the dsDNA molecule and (ii) a second 5' overhang DNA sequence of at least 10 nucleotides on a second strand of the dsDNA molecule, wherein the first overhang and the second overhang do not anneal together, and wherein each overhang anneals to one overhang of a second and a third dsDNA molecule, respectively; preparing a second dsDNA molecule containing (i) a first 5' overhang DNA sequence of at least 10 nucleotides on a first strand of the dsDNA molecule and (ii) a second 5' overhang DNA sequence of at least 10 nucleotides on a second strand of the dsDNA molecule, wherein the first overhang and the second overhang do not anneal together, and wherein each overhang anneals to one overhang of a third and a fourth dsDNA molecule, respectively; and combining the first dsDNA molecule and the second dsDNA molecule under conditions that permit DNA annealing of the 5' overhang sequences, thereby assembling the plurality of dsDNA molecules.

In some embodiments, the first and second dsDNA molecules are combined with at least one additional dsDNA molecule. In some embodiments, the first and second 5' overhangs are at least 20 nucleotides in length, at least 30 nucleotides in length, at least 40 nucleotides in length, or at least 50 nucleotides in length.

In some embodiments, the methods further include preparing a double stranded linear nucleic acid vector containing (i) a first 5' overhang DNA sequence of at least 10 nucleotides on a first strand of the vector and (ii) a second 5' overhang DNA sequence of at least 10 nucleotides on a second strand of the vector, wherein the first overhang and the second overhang do not anneal together, and wherein each overhang anneals to one overhang of two different dsDNA molecules; and combining the assembled dsDNA molecules of any one of claims 1-6 with the vector under conditions that permit DNA annealing, wherein the assembled dsDNA molecules comprise overhangs that anneal to the overhangs of the vector, thereby assembling the vector and the assembled dsDNA molecules.

In some embodiments, the methods further include probing one or more of the overhang sequences of assembled dsDNA molecule to select correctly assembled dsDNA molecules. In other embodiments, the methods further include probing the overhang sequences of assembled dsDNA molecule to confirm the structure of the assembled dsDNA molecule.

According to another aspect of the invention, methods of preparing a dsDNA molecule are provided. The methods include providing a circular DNA vector comprising a vector backbone VB and a polynucleotide P-X-S, wherein P is a prefix nucleic acid sequence and S is a suffix nucleic acid sequence, each comprising one or more enzyme recognition sites, and X is a DNA part of interest; linearizing the circular DNA vector with one or more enzyme that cleaves one or more enzyme recognition sites in the suffix to produce a linear double-stranded (ds) DNA having a 5' overhang at each end of the dsDNA; ligating to the 5' overhang of the suffix a first oligonucleotide having a length of at least 20 nucleotides; removing the vector backbone from the linear dsDNA with one or more enzyme that cleaves one or more enzyme recognition sites in the prefix, producing a 5' overhang; and ligating to the 5' overhang of the prefix a second oligonucleotide having a length of at least 20 nucleotides, thereby preparing a dsDNA molecule.

In some embodiments, the DNA element X is selected from the group consisting of: a terminator sequence, a ribosome binding site sequence, a protein coding sequence, a reporter sequence, a signaling sequence, a primer sequence, and a regulatory sequence.

In some embodiments, the enzymes are selected from the group consisting of EcoRI, XbaI, PstI, and SpeI. In other embodiments, the enzymes are selected from I-AniI, I-CeuI, I-ChuI, I-CpaI, I-CpaII, I-CreI, I-DmoI, H-DreI, I-HmuI, I-HmuII, I-LlaI, I-MsoI, PI-PfuI, PI-PkoII, I-PorI, I-PpoI, PI-PspI, I-ScaI, I-SceI, PI-SceI, I-SceII, I-SecIII, I-SceIV, I-SceV, I-SceVI, I-SceVII, I-Ssp6803I, I-TevI, I-TevII, I-TevIII, PI-TliI, PI-TliII, I-Tsp06II, and I-Vdi141I.

In some embodiments, the methods further include probing the prefix and/or the suffix of the newly assembled DNA molecule to select correctly assembled dsDNA molecules. In other embodiments, the methods further include probing the prefix, then probing the suffix of the newly assembled DNA molecule to confirm the structure of the assembled dsDNA molecule.

In some embodiments of all of the foregoing methods, the method excludes polymerase chain reaction (PCR) purification.

In some embodiments of all of the foregoing methods, the method excludes antibiotic selection.

In some embodiments of all of the foregoing methods, the method is automated.

According to another aspect of the invention, nucleic acid molecules, such as DNA molecules, are provided. The nucleic acid molecules include a double-stranded DNA; a first 5' overhang of at least 10 nucleotides in length located at one end of the DNA; and a second 5' overhang of at least 10 nucleotides in length located at the other end of the DNA. In some embodiments the double-stranded DNA is a standard DNA part.

According to another aspect of the invention, nucleic acid molecules, such as DNA molecules, are provided. The nucleic acid molecules include a first biotinylated oligonucleotide of at least 10 nucleotides in length, wherein the first oligonucleotide is not phosphorylated and is attached to a bead. In some embodiments, the bead is a streptavidin-coated bead. In some embodiments, the nucleic acid molecules further include a second oligonucleotide of at least 10 nucleotides in length annealed to the first oligonucleotide such that there is a 5' overhang opposite the bead.

According to another aspect of the invention, double-stranded DNA molecules are provided that include a nucleic acid of interest flanked by a prefix sequence and suffix sequence, each of the prefix sequence and the suffix sequence comprising one or more homing enzyme restriction sites. In some embodiments, the DNA molecules further include an origin of replication. In some embodiments, the DNA molecules further include an antibiotic resistance selection marker. In some embodiments, the DNA molecules are attached to a bead or a DNA molecule comprising a bead.

According to another aspect of the invention, collections of two or more of the DNA molecules are provided. The collections include two or more of any of the DNA molecules described herein.

According to another aspect of the invention, kits including one or more containers containing two or more of any of the DNA molecules described herein.

DETAILED DESCRIPTION OF THE INVENTION

The methods and compositions provided herein, in certain aspects, overcome previous limitations by using magnetically-controlled DNA probes that anneal directly to standard DNA prefix and suffix regions to both isolate and assemble new DNA parts without intermediate cloning steps. In some aspects, the methods provided herein reduce construction time, minimize mutations, and support intermediate constructs that may be toxic to a cell or otherwise difficult to grow.

DNA Construction

Aspects provided herein enable rapid and automated assembly of multiple arbitrary length DNA fragments or parts. A DNA part may be any DNA sequences of defined structure and function. Examples include, but are not limited to, terminator sequences, ribosome binding site (RBS) sequences, protein coding sequences, reporter sequences, signaling sequence, primer sequence, and regulatory sequences or transcriptional control sequences.

A "terminator sequence" refers to a sequence typically located at the end of a gene or operon to stop transcription.

An "RBS sequence" refers to a sequence that, when transcribed, is a segment of the 5' (upstream) part of an mRNA molecule that binds to the ribosome to position the message correctly for the initiation of translation.

A "protein coding sequence" refers to sequence information needed to create functional protein (polypeptide).

A "reporter sequence" refers to a sequence encoding a product that is measurable, for example, a fluorescent protein or colorimetric enzyme. Examples include β-galactosidase, chloramphenicol acetyltransferase, β-glucuronidase, and green or red fluorescent protein (GFP or RFP).

A "signaling sequence" refers to a sequence encoding a signal peptide (e.g., a ~3-60 amino acids long peptide chain that directs the transport of a protein).

A "primer sequence" refers to a strand of nucleic acid that serves as a starting point for DNA synthesis.

A "regulatory sequence" or "transcriptional control sequence" refers to a binding region for RNA polymerase, for example, a promoter or enhancer sequence. In some embodiments, a regulatory sequence may be constitutive, while in other embodiments, it may be inducible.

A DNA part may be provided as a linear structure or it may be part of a DNA plasmid vector. A "plasmid vector" is a circular, double-stranded DNA molecule that may contain a few thousand base pairs that replicate within the cell independently of chromosomal DNA.

In some embodiments, a plasmid is a bacterial plasmid (derived or isolated from bacteria). A bacterial plasmid may be derived from an organism selected from *Acetobacter* spp., *Acidithiobacillus* spp., *Acinetobacter* spp., *Aeromonas* spp., *Arcanobacterium* spp., *Agrobacterium* spp., *Alcaligenes* spp., *Aquifex* spp., *Arthrobacter* spp., *Azotobacter* spp., *Bacillus* spp., *Bifidobacterium* spp., *Borrelia* spp., *Chromobacterium* spp., *Citrobacter* spp., *Clostridium* spp., *Comamonas* spp., *Corynebacterium* spp., *Deinococcus* spp., *Enterobacter* spp., *Erwinia* spp., *Erysipelothrix* spp., *Escherichia* spp., *Flavobacterium* spp., *Francisella* spp., *Fusobacterium* spp., *Geobacter* spp., *Geobacillus* spp., *Gluconobacter* spp., *Halobacterium* spp., *Helicobacter* spp., *Lactobacillus* spp., *Lactococcus* spp., *Marinococcus* spp.,

*Methanobacterium* spp., *Methanococcus* spp., *Microcystis* spp., *Microlunatus* spp., *Mycobacterium* spp., *Pseudomonas* spp., *Pantoea* spp., *Ralstonia* spp., *Rhizobium* spp., *Rhodococcus* spp., *Ruminococcus* spp., *Serratia* spp., *Saccharopolyspora* spp., *Stenotrophomonas* spp., *Sinorhizobium* spp., *Saccharopolyspora* spp., *Staphylococcus* spp., *Streptococcus* spp., *Streptomyces* spp., *Sulfolobus* spp., *Synechococcus* spp., *Synechocystis* spp., *Thermus* spp., *Thiobacillus* spp., *Vibrio* spp., *Xanthomonas* spp., *Xyella* spp., *Yersinia* spp., *Zygosaccharomyces* spp., or *Zymonas* spp.

Examples of bacterial plasmids include SUN Plasmid pRAY, pTi-SAKURA, pAP1, ece1, pAC5, pXO2, pRBH1, pPL10, pTA1040, pTA1015, pTA1060, p1414, pSTK1, pBMB9741, pTX14-3, pTX14-1, pBMB2062, pCIBb1, RK2,RP1,RP4,R18,R68, 1p17, 1p25, 1p28-1, 1p28-2, 1p28-3, 1p28-4, 1p 36, 1p 38, 1p 54, cp26, cp9, cp32-1, cp32-3, cp32-4, cp32-6, cp32-7, cp32-8, cp32-9, 1p21, 1p56, 1p5, pLeu-Sg, pLeu-Dn, pOM1, pCpA1, pCL1, pSOL1, pSOL12, MCF-1 indigenous plasmid, pPT1, R-plasmid pAG1, pAM330, pSR1, pXZ10145.1, MP1, CP1, R751, pPIGDM1, pSW200, pAP1, C1oDF13, Co1A, Co1E1, Co1Ib-P9, pECO29, pKL1, NTP16, pO157, pOSAK1, R100, mini Rts1, pFL1, pOM1, pPA52, pHGN1, pNRC100, pHPM180, pHPM186, pHPO100, pHP489, pWS58, pLH1, pLJ1, pAH33, pCIS3, pMRC01, pIL105, pLTK2, pGT232, pPL1, pME2200M, pME2001, pFV1, pFZ1, pURB500, pMA2, small pMA1, pTA144 Dw, pTA144 Up, pJD4, pAYL, pAYS, pUCD5000, pPZG500, pAB2, pIG1, pMD136, pPF1, pPBS1, Pp6427, Pp6859, pRAM4, pGT5, pMBCP, pJTPS1, NGR234, pRM21, pCFC1, pCFC2, pBAW301, pBERT, pSC101, pSR1, pNL1, pSK6, pSK3, pKH6, J3358, pKH7, pC221, pUB110, pC194, pLUG10, pGB354, pSSU1, pER35, pER36, pSCL, pSA1.1, pSNA1, pSN22, pJV1, pRN1, pRN2, pMA4, pTF4.1, pSA19, pXF868, pYVe227, pPCP1, pCD1, pMT1[100984 bp, pCD1, pMT-1, pYC, pZMO1, pSB2, and pSM1 FLP. In certain embodiments, the plasmid is derived from a eukaryotic organism such as *Saccharomyces cerevisiae*.

In certain aspects, arbitrary DNA for assembly is performed by "direct conversion," followed by "double probing" (each defined below). In some embodiments, the methods described herein facilitate high fidelity assembly with the prepared DNA parts. In certain embodiments, arbitrary DNA assembly may be performed by direct conversion without using double probing. Similarly, in some embodiments, double probing may be used without direct conversion. In particular embodiments, however, the serial combination of the two allow for robust DNA assembly.

Conversion of Standard Parts to Self-Assembling Parts

Described herein are methods of transforming a standard DNA part (e.g., from a library of standard DNA or genetic circuits) that typically has a universal prefix and suffix into a single self-assembling part via the addition of a designer prefix and suffix segment. A "prefix" as used herein refers to a DNA sequence flanking a nucleic acid (e.g., protein coding sequence) of interest at the 5' end of the nucleic acid. A "suffix" refers to a DNA sequence flanking the nucleic acid at its 3' end. In embodiments, a prefix and/or suffix may have one more enzyme recognition sites (also referred to as restriction sites), which are cleaved (cut) by restriction enzymes.

A restriction enzyme may be a Type I, Type II, Type III, or Type IV enzyme. Type I enzymes (EC 3.1.21.3) cleave at sites remote from recognition site, typically require both ATP and S-adenosyl-L-methionine to function, and are multifunctional proteins with both restriction and methylase (EC 2.1.1.72) activities. Type II enzymes (EC 3.1.21.4) cleave within or at short specific distances from recognition site, most require magnesium, and are single function (restriction) enzymes independent of methylase. Type III enzymes (EC 3.1.21.5) cleave at sites a short distance from recognition site, typically require ATP, S-adenosyl-L-methionine can stimulate the reaction but is not required, and they exist as part of a complex with a modification methylase (EC 2.1.1.72). Type IV enzymes target methylated DNA. In particular embodiments, the restriction enzymes described herein are Type II enzymes. Examples of Types II restriction enzymes include, but are not limited to EcoRI, EcoRII, BamHI, HindIII, TaqI, NotI, HinfI, Sau3, APovII, SmaI, HaeIII, HgaI, AluI, EcoRV, EcoP151, KpnI, PstI, SacI, SalI, ScaI, SpeI, SphI, StuI, and XbaI.

A restriction enzyme may also be a homing enzyme. A "homing enzyme" (or homing endonuclease) refers a restriction enzymes encoded by introns or inteins. Examples include I-AniI, I-CeuI, I-ChuI, I-CpaI, I-CpaII, I-CreI, I-DmoI, H-DreI, I-HmuI, I-HmuII, I-LlaI, I-MsoI, PI-PfuI, PI-PkoII, I-PorI, I-PpoI, PI-PspI, I-ScaI, I-SceI, PI-SceI, I-SceII, I-SecIII, I-SceIV, I-SceV, I-SceVI, I-SceVII, I-Ssp6803I, I-TevI, I-TevII, I-TevIII, PI-TliI, PI-TliII, I-Tsp061I, I-Vdi141I, PI-PspI, and PI-IsceI. Homing endonuclease recognition sequences are typically long enough to occur randomly only with a very low probability (e.g., approximately once every $7 \times 10^{10}$ nucleotides) and, in some cases, are found in only one instance per genome.

DNA Oligonucleotides—Prefix, Suffix, and Probe Design

A single-stranded prefix, suffix, or probe oligonucleotide (e.g., single-stranded stretch of DNA), in certain embodiments, is of sufficient length to have a melting temperature ($T_m$) similar to its annealing temperature. In certain embodiments, an oligonucleotide's $T_m$ is at least higher than the temperature at which the DNA assembly reaction is performed, e.g., higher than room temperature. In some embodiments, the Tm of an oligo may be about 45° C., 50° C., 55° C., 60° C., 65° C., 70° C., 75° C., or higher. In some instances, depending on the DNA assembly reaction temperature, the Tm of the oligos may be lower than 45° C.

In certain embodiments, the length of an oligonucleotide (oligo) may be about 10 to about 50, about 10 to about 100, or about 10 to about 500, or more nucleotides in length. For example, the oligo may be at least 10, at least 20, at least 30, at least 40, at least 50, at least 60, at least 70, at least 80, at least 90, at least 100, at least 200, at least 300, at least 400, or at least 500 nucleotides in length. In certain embodiments, an oligo described herein is about 20, about 30, about 40, or about 50, or about 60 nucleotides long. In specific embodiments, the oligos described herein are about 40 nucleotides long.

In some embodiments, the oligos described herein are biotinylated (i.e., one or more biotin molecule(s) is covalently attached to the oligo). In some embodiments, the oligos described herein may be attached to beads, also referred to as magnetic beads. In certain embodiments, the beads are coated (covered) in streptavidin or avidin.

The direct conversion methods described herein can achieve direct automated assembly of DNA, in many instances, providing "building blocks" for the described assembly methods. Below are methods of converting existing standard DNA parts into self-assembling parts.

Direct Conversion from BioBrick™ Standard Parts

The methods described herein may be used to convert, for example, the standard BioBricks™ Foundation RFC 10 part (Knight, T. (2003), *Idempotent Vector Design for Standard Assembly of Biobricks*, MIT Synthetic Biology Working Group) into a self-assembling part through the ligation of long (e.g., at least 10, at least 20, at least 30, or at least 40 nucleotides) single-stranded overhangs to restriction sites in standard prefix and suffix sequences. FIGS. 17 and 18 depict one embodiment of a method for preparing a self-assembling DNA part (molecule). FIG. 17 shows the steps adding (e.g., ligating) an overhang to a SpeI restriction site in the suffix, while FIG. 18 shows the steps adding an overhang to the XbaI restriction site in the prefix.

An optional, preferred component of the methods described herein is the use of double probing. Double probing is a sequence-specific selection or enrichment method that removes molecules that do not anneal to both probes, and keeps molecules that do anneal.

Production of Self-Assembling DNA Units Using Homing Enzymes

Described herein are standard DNA parts, and related methods, produced using one or more homing enzymes ("meganucleases") with long and therefore rare recognition sites in the prefix and suffix. In certain embodiments, use of homing enzymes may provide more flexibility in the design of the DNA part itself and/or its subsequent utilization in downstream processes. In one embodiment, a standard DNA part described herein, may comprise a restriction site for I-AniI, I-CeuI, I-ChuI, I-CpaI, I-CpaII, I-CreI, I-DmoI, H-DreI, I-HmuI, I-HmuII, I-LlaI, I-MsoI, PI-PfuI, PI-PkoII, I-PorI, I-PpoI, PI-PspI, I-ScaI, I-SceI, PI-SceI, I-SceII, I-SecIII, I-SceIV, I-SceV, I-SceVI, I-SceVII, I-Ssp6803I, I-TevI, I-TevII, I-TevIII, PI-TliI, PI-TliII, I-Tsp061I, I-Vdi141I, PI-PspI, or PI-IsceI. In certain embodiments, a meganuclease-based standard DNA part ("MegaBrick") includes a restriction site for I-SceI in the prefix and I-CeuI in the suffix (or I-SceI in the suffix and I-CeuI in the prefix) surrounding the DNA part as follows:

[I-SceI prefix|PART|I-CeuI suffix].

Some variability in homing enzyme recognition sites is possible. One set of recognition sites and resulting overhangs from the New England BioLabs (NEB) website is:

```
I-SceI recognition site:
                                   (SEQ ID NO: 7)
5' AGTTACGCTAGGGATAACAGGGTAATATAG 3'

I-SceI overhangs:
ATAA, TTAT

I-CeuI recognition site:
                                   (SEQ ID NO: 8)
5' CGTAACTATAACGGTCCTAAGGTAGCGAA 3'

I-CeuI overhangs:
CTAA, TTAG
```

Unlike TypeII enzymes, for example, homing enzymes have non-palindromic overhangs, so, in some embodiments, only two enzymes may be used to construct a self-assembling DNA molecule. In certain embodiments, the 4-nucleotide non-palindromic overhang provides flexibility because (1) the long (e.g., 18-base pair) recognition site reduces the possibility of collision with a sequence in the original DNA, and (2) the non-palindromic overhang permits combined restriction enzyme and overhang ligation steps in a single pot (e.g., tube or well) reaction, optionally followed by the double probe method to enrich for the correct product (self-assembling molecules).

In some embodiments, the final self-assembled DNA conform to a "MegaBrick" standard. In some instances, in order for the final assembly to be idempotent, the meganuclease (homing enzyme) restriction sites are reintroduced on separate DNA parts annealed from two homologous oligonucleotides with long (e.g., at least 10 nucleotides) overhangs created. For example:

[I-scel-part|part1|part2|part2|I-ceul-part].

Simultaneous Joining and Conversion from Multiple Standard Parts

Also provided herein are methods of assembling (e.g., ligating and/or annealing) multiple (standard) DNA parts into a single DNA molecule (e.g., genes, gene circuits). In certain embodiments, the methods described herein can be used to assemble multiple DNA parts simultaneously to produce longer or compound self-assembling parts. In some instances, the methods provide intermediate assembled parts allowing for faster/less complex future assemblies (e.g., for gene circuits). The number of parts that can be assembled at once into a new self-assembling molecule is a function of the assembly standard. In some embodiments, 2 to 5, 2 to 10, 2 to 20, 2 to 30, 2 to 40, or 2 to 50 parts can be assembled. In some embodiments 2, 3, 4, 5, 6, 7, 8, 9, 10, 11, 12, 13, 14, 15, 16, 17, 18, 19, 20, or more parts can be assembled. Examples of multiple DNA part assembly are, as follows:

EXAMPLE (1)-For assembly of multiple BioBrick™ parts using BioBrick RFC10, at least two parts can be ligated and converted into a self-assembling molecule and its assembly verified using the double probe method, described herein:

[Prefix-Part 1]+[Part 2-Suffix].

EXAMPLE (2)-In some embodiments, multiple parts can be assembled with TypeIIS enzymes and unique 4-nucleotide intersections. In certain embodiments, the methods provided herein exclude or omit standard molecular cloning methods such as antibiotic resistance or screening selection methods (e.g., see Weber, E. et al. *PLoS ONE*, 6, e16765, 2011). In some instances, the double probing methods described herein provide for the ligation and selection of a multiple parts into a self-assembling molecule in the following form:

[PrefixOverhang:Part1:Part2: . . . PartN:SuffixOverhang].

EXAMPLE (3)-In some embodiments, two or more self-assembling parts can be annealed and the new construction double probed in order to remove unwanted/unannealed products. In some embodiments, the assembled molecule will be a larger self-assembling part, ready for self-assembly into even larger molecules, and in some instances, at high efficiencies.

Double Probing

Double probing may be defined herein as a method in which two identifiable or recoverable probes are attached (e.g., ligated or annealed) to both ends of a target sequence in order to verify, optimize, and/or enrich a given DNA target sequence. In some embodiments, double probing provides a higher level of sequence and assembly validation as compared to current strand-end hybridization methods. In certain embodiments, double probing is used to construct large gene circuits. In some embodiments, double probing increases yield of each intermediate and end-product DNA molecule.

Probing with Two Probes

In certain aspects, the double probing method comprises first probing one overhang of an assembled DNA molecule (e.g., the prefix), then probing a different overhang of the assembled DNA molecule (e.g., the suffix) to verify that the assembled molecule is correct (e.g., to confirm the structure of the molecule, including the order of the assembled parts). In some aspects, the double probing method is used to select or capture correctly assembled molecules. For example, when a DNA molecule is assembled using two long (e.g., at least 10 nucleotide) overhangs, double probing selects for correct molecules and rejects incorrect molecules. An another example, when converting two or more standard parts into self-assembling parts, double probing can verify that the long overhangs are present on selected assembled molecules. Double probing can also verify the accuracy and structure of intermediate parts because any parts required to assemble a larger part/molecule will remain attached to the probe when probed from either end of the molecule.

Probing with Temporary Overhangs

In some aspects, provided herein are methods of preparing self-assembling DNA parts having temporary single-stranded DNA overhangs. In some embodiments, the temporary overhangs may be double probed.

In some embodiments, temporary single-stranded DNA overhangs can be created with an exonuclease which removes or "chews" DNA bases from either its 3' or the 5'end. This process may be referred to, and is known in the art, as "chewback." When no dNTPs are present T4 DNA Polymerase (NEB MO203), for example, acts as an exonuclease and chews back from the 3' end of the DNA. As another example, T5 Exonuclease chews back from the 5' end of the DNA. In one embodiment, a temporary overhang is prepared by permitting chewback by a T4 or T5 for a defined period of time, then inactivating the chewing enzyme (e.g., with heat inactivation). Similar to the fixed overhangs described herein, in some embodiments, temporary overhangs can be used in any one of the double probing methods provided herein to verify that two DNA parts are correctly joined. In some embodiments, the temporary overhangs described herein may also be used for sequence-specific purification.

In certain embodiments, an advantage of temporary overhangs is that after probing, removed DNA can be replaced and the integrity of the original double-stranded DNA restored or repaired. In some embodiments, the introduction of extraneous scar sequences into an assembled DNA molecule can be avoided by using temporary overhangs. To eliminate the overhang, it may be necessary to add complementary DNA to an assembly reaction. In some embodiments, T4 DNA polymerase (with dNTPS), Taq polymerase, or an error correcting polymerase such as Pfx (Invitrogen®) may be used to eliminate a temporary overhang. In other embodiments, a temporary overhang may be eliminated by annealing to the overhang a single-stranded oligonucleotide cap complementary to the chewed back region.

Double probing with temporary overhangs, in certain embodiments, enables multistep ligation-based assembly without intermediate in vivo cloning/screening steps (see Results, e.g., FIG. 8-12).

As an example, for BioBrick™ RFC 10 (Draft standard for BioBrick™ biological parts), temporary overhangs can be used to probe both prefix and suffix of the DNA part (FIG. 13), as well as either end of the backbone (FIG. 16). This method, in some instances, may be used to purify parts from backbones without the use of gel extraction or overhang ligation.

Applications

Simplifying Existing Workflows

The field of synthetic biology covers a broad range of application areas, from food and energy, to the environment, to health and medicine, and even to manufacturing of new materials. In certain embodiments, the methods and compositions provided herein may facilitate biological engineering and may be used by a diverse group of people. In particular embodiments, the methods and compositions described herein may be used to explore the molecular design space in the fields of biotechnology and microbiology, for example, in medicine and agriculture.

Large Scale Assembly of Genes/Gene Circuits

As described herein, double probing enables the robust assembly of large scale DNA molecules. In certain instances, the methods and compositions described herein may be used for the construction of large genes, and even small genomes.

Automated Assembly

One application of the methods and compositions described is the automation of DNA assembly workflows. In some embodiments, the methods described herein are performed in liquid phase, or on soluble magnetic beads between common operating temperatures (e.g., 10° C. to 80° C. Therefore, in some instances, the DNA assembly steps are executable on current commercially available liquid handling robots.

Additional Embodiments

In some aspects, provided herein are beads with standard probes and complementary overhangs for creating customized parts from proprietary or other DNA sequences available to the end user.

In other aspects, provided herein are libraries of self-assembling parts with pre-designed long (e.g., at least 10 nucleotides) overhangs. In some embodiment, these parts can be provided as aliquots of DNA, either in tubes, microplates of size 96, 384, 1536, 3456, 9600, or other formats as available, in microfluidic chips, or hybridized to DNA microarrays and photo-released.

In certain other aspects, protocols on a standard liquid handling robot or a specialized device or machine for processing magnetic beads are provided. In some aspects, software is provided for designing new unique overhangs. In yet other aspects, complete machines/devices for designing and automating DNA part assembly are provided. For example, in some embodiments, bead handling may be performed using a Tecan Evo 150 liquid handler.

EXAMPLES

Methods & Materials
Molecular Biology

BioBrick Assembly kit (EO546) including EcoRI, XbaI, SpeI, PstI, T4 DNA ligase were purchased from New England BioLabs (NEB). These enzymes may also be purchased separately and are generally available from other vendors. NEB also supplies homing endonucleases I-SceI (R0694) and I-CeuI (R0699). AccuPrime Pfx Supermix from Invitrogen (Life Technologies, Carlsbad Calif.) was used for PCR verification of long overhang additions. Miniprep of DNA was done using Qiagen Qiaprep Spin Miniprep Kit. Some minipreps were automated on Qiagen Qiacube using the same miniprep kit.

Architecture of Anchors

The next section shows sequences for anchors if prefix and suffix are BioBrick RFC10 (compatible with XbaI/SpeI 4bp sites). Constraints on anchors.

1. Should not contain forbidden cutsites
2. Ligation of 4 bp overhang should not introduce either XbaI or SpeI cutsite (special case for backbone)
3. Should be long enough to easily anneal (e.g. 40 bp)
4. Should be unique versus other anchors and complementary to one other prefix/suffix Details of Anchor Sequences In both conversion and probing methods, oligonucleotide anchor sequences capable of annealing to complementary overhangs of around 40 bp were used. Overhangs and anchors may be shorter so long as the melting temperature (Tm) is in a similar range to that used for PCR primers (for example, 50-70° C.). Longer overhangs are more effective but are also more costly. Similar to primers, secondary structure and hairpin formation should be minimized. While the first and last bases in the overhang must match the cutsites used for ligation to the standard parts, the interior region can be composed of a large range of sequences so long as the following conditions are met:

1. an anchor and the overhang it anneals to should be complementary;

2. overhangs designed to self-assemble should be complementary;

3. all other anchor and overhang combinations should be non-homologous;

4. anchor and overhang sequences should not contain the forbidden restriction enzyme cutsites defined by the standard being converted (for example, for RFC10 this would be EcoRI, XbaI, SpeI, PstI).

In one embodiment, we choose sequences as follows:
Nine unique sequences that can be used for overhangs based on combinations of 12 mer words in Shortreed, et al., A thermodynamic approach to designing structure-free combinatorial DNA word sets. Nucl. Acids Res. 33(15): 4965-4977 doi:10.1093/nar/gki812.

```
1 =
                                          (SEQ ID NO: 9)
CACCATCTACATAACACCTCAATTACACCATTCATT

2 =
                                         (SEQ ID NO: 10)
ACCAATTCTCTCCACCTTTATCCTACCAAAATTCCT

3 =
                                         (SEQ ID NO: 11)
TTCCTTCTCTTCCACCAAATTTCAACACACTAACAT

4 =
                                         (SEQ ID NO: 12)
TCCTATCTCACTAACCAACATCATCTCCATACATCA

5 =
                                         (SEQ ID NO: 13)
TTCATACCTCACAAAACCTCCTTTCTCCTTCTCATT

6 =
                                         (SEQ ID NO: 14)
CTCTTCACTACACACCATATTCCTCTCCAAATACCT

7 =
                                         (SEQ ID NO: 15)
ACACATTTTCACACCAATTCCATTAACCATCATCAA

8 =
                                         (SEQ ID NO: 16)
CAACACTTTCAACACTCAATACCTACAACTCTACTC

9 =
                                         (SEQ ID NO: 17)
TTTCTTTCACCAAACCACTTTCATACAATCTCACAT
```

DNA sequence examples for first two unique overhangs and BioBrick RFC10 conversion:

```
J85330,
                                         (SEQ ID NO: 18)
CTAGACACCATCTACATAACACCTCAATTACACCATTCATTA,
Multiway BioBrick 1-prefix-fwd J85331,
                                         (SEQ ID NO: 19)
CTAGTAATGAATGGTGTAATTGAGGTGTTATGTAGATGGTGTCTAG/
3BioTEG/,Multiway BioBrick 1-prefix-rev J85332,
                                         (SEQ ID NO: 20)
CTAGACACCATCTACATAACACCTCAATTACACCATTCATTACTAG/
3BioTEG/,Multiway BioBrick 1-suffix-fwd J85333,
                                         (SEQ ID NO: 21)
CTAGTAATGAATGGTGTAATTGAGGTGTTATGTAGATGGTGT,
Multiway BioBrick 1-suffix-rev J85334,
                                         (SEQ ID NO: 22)
CTAGAGCCAATTCTCTCCACCTTTATCCTACCAAAATTCCTA,
Multiway BioBrick 2-prefix-fwd J85335,
                                         (SEQ ID NO: 23)
CTAGTAGGAATTTTGGTAGGATAAAGGTGGAGAGAATTGGCTCTAG/
3BioTEG/,Multiway BioBrick 2-prefix-rev J85336,
                                         (SEQ ID NO: 24)
CTAGAGCCAATTCTCTCCACCTTTATCCTACCAAAATTCCTACTAG/
3BioTEG/,Multiway BioBrick 2-suffix-fwd J85337,
                                         (SEQ ID NO: 25)
CTAGTAGGAATTTTGGTAGGATAAAGGTGGAGAGAATTGGCT,
Multiway BioBrick 2-suffix-rev
```

Phosphorylated Anchor Complements:

```
J85360,
                                         (SEQ ID NO: 26)
/5Phos/CTAGACACCATCTACATAACACCTCAATTACACCATTCATTA,
Multiway BioBrick 1-prefix-fwd-phos J85363,
                                         (SEQ ID NO: 27)
/5Phos/CTAGTAATGAATGGTGTAATTGAGGTGTTATGTAGATGGTGT,
Multiway BioBrick 1-suffix-rev-phos J85364,
                                         (SEQ ID NO: 28)
/5Phos/CTAGAGCCAATTCTCTCCACCTTTATCCTACCAAAATTCCTA,
Multiway BioBrick 2-prefix-fwd-phos J85367,
                                         (SEQ ID NO: 29)
/5Phos/CTAGTAGGAATTTTGGTAGGATAAAGGTGGAGAGAATTGGCT,
Multiway BioBrick 2-suffix-rev-phos
```

Note: non-phosphorylated overhangs can only be ligated in vitro with the addition of T4 Polynucleotide kinase (for example NEB M0201S), while either version will be ligated in vivo, after transformation. One or the other version may be preferred depending of oligo and enzyme costs.

In some embodiments, as special type of anchor can be used to preserve XbaI, SpeI cutsites for backbone overhang ligations (a single base is different). Alternatively, re-introduction of cutsites is done on separate self-assemblable parts with long overhangs. The goal in these embodiments is to preserve idempotency, i.e., so the resulting part will also be a BioBrick having proper flanking restriction enzyme cutsites.

Exemplary Design of Probes and Overhangs for I-SceI and I-CeuI Flanked Standard Parts.

Two Unique Overhangs:

1 =
(SEQ ID NO: 30)
CACCATCTACATAACACCTCAATTACACCATTCATT

2 =
(SEQ ID NO: 31)
ACCAATTCTCTCCACCTTTATCCTACCAAAATTCCT

1rc =
(SEQ ID NO: 32)
AATGAATGGTGTAATTGAGGTGTTATGTAGATGGTG

2rc =
(SEQ ID NO: 33)
AGGAATTTTGGTAGGATAAAGGTGGAGAGAATTGGT

70/71-IsceI-----IceuI-72/73

74/75-Iscel-----IceuI-76/77

J85370,
(SEQ ID NO: 34)
/5Phos/CACCATCTACATAACACCTCAATTACACCATTCATT ATAA,
1-prefix-fwd J85371,
(SEQ ID NO: 35)
AATGAATGGTGTAATTGAGGTGTTATGTAGATGGTG/3BioTEG/,
1-prefix-rev J85372,
(SEQ ID NO: 36)
CACCATCTACATAACACCTCAATTACACCATTCATT/3BioTEG/,
1-suffix-fwd J85373,
(SEQ ID NO: 37)
/5Phos/AATGAATGGTGTAATTGAGGTGTTATGTAGATGGTG TTAG,
1-suffix-rev J85374,
(SEQ ID NO: 38)
/5Phos/ACCAATTCTCTCCACCTTTATCCTACCAAAATTCCT ATAA,
2-prefix-fwd J85375,
(SEQ ID NO: 39)
AGGAATTTTGGTAGGATAAAGGTGGAGAGAATTGGT/3BioTEG/,
2-prefix-rev J85376,
(SEQ ID NO: 40)
ACCAATTCTCTCCACCTTTATCCTACCAAAATTCCT/3BioTEG/,
2-suffix-fwd J85377,
(SEQ ID NO: 41)
/5Phos/AGGAATTTTGGTAGGATAAAGGTGGAGAGAATTGGT TTAG,
2-suffix-rev Pairs or anchoring probes and complementary overhangs are J85330/J85331; J85332/J85333; J85334/J85335; J85336/J85337; J85360/J85331; J85332/J85363; J85364/J85335; J85336/J85367; J85370/J85371; J85372/J85373; J85374/J85375; and J85376/J85377.

Overhangs that are complementary are: J85330/J85333; J8334/J85337; J85360/J85363; J85364/J84367; J85370/J85373; and J8374/J85377.

The term "/5Phos/" denotes a phosphorylated oligo and the term "/3BioTEG/" denotes a 3' biotinylated oligo as ordered from IDTDNA.

When long overhangs are designed to ligate to short 5'overhangs, the long overhang must include matching short overhang sequences on either end. When ligating to a recessed 5' end, only the ligating must be complementary to the short overhang.

It is important not to phosphorylate the 5' end of the biotinylated anchor probe so that during ligation no permanent connection is made to DNA that can be easily be removed from the bead.

Example assemblable part that can be created are J85370: part:J85377 or J85374:part:J85373. Note that between the overhang and the part is a dsDNA scar roughly equivalent to half the endonuclease cutsite.

Additional anchor sequences for use with temporary overhangs created by 3' and 5' chewback of BioBrick RFC10 prefix and suffix, part and backbone:

J85310,
(SEQ ID NO: 42)
/5Phos/CTAGAAGCGGCCGCGAATTC/ideoxyU/AAGAAAC/
3BioTEG/,5P-Prefix(rc)-BTEG ending with X end J85311,
(SEQ ID NO: 43)
/5Phos/TCTAGAAGCGGCCGCGAATTC/ideoxyU/AAGAAAC/
3BioTEG/,5P-Prefix(rc)-BTEG ending with X site J85312,
(SEQ ID NO: 44)
/5Phos/TACTAGTAGCGGCCGCTGCAG/ideoxyU/AAGAAAC/
3BioTEG/,5P-Suffix(rc)-BTEG J85317,
(SEQ ID NO: 45)
/5BioTEG/GTTTCTTCCTGCAGCGGCCGCTAC, 5-BTEG-Suffix
capture J85318,
(SEQ ID NO: 46)
/5BioTEG/CTGCAGCGGCCGCTA/ideoxyU/TAGTA, 5-BTEG-
Suffix short create overhang J85319,
(SEQ ID NO: 47)
/5BioTEG/GTTTCTTCCTGCAGCGGCCGCTA/ideoxyU/TAGTA,
5-BTEG-Suffix long create overhang J85320,
(SEQ ID NO: 48)
/5AmMC6/GTTTCTTCGAATTCGCGGCCGCTTCTAGA, 5-C6-Prefix J85324 is used to probe the end of the backbone that connects to the prefix of PSB1A2 if 3' chewed, for example with T4 DNA Polymerase. J85325 is used to probe the end of the backbone that connects to the suffix when 5' chewed, for example with T5 Exonuclease.

J85324,
(SEQ ID NO: 49)
AAA AAA TCC TTA GCT TTC GCT AAG GAT GAT TTC TGG
AAT T/3BioTEG/, 3B backbone-prefix J85325,
(SEQ ID NO: 50)
/5BioTEG/TG CAG GCT TCC TCG CTC ACT GAC TCG CTG
CGC TCG GTC GT, 5B backbone-suffix An efficient procedure for separating a BioBrick part from its backbone is to cut with EcoRI (PstI), chew with T4 DNA polymerase (T5 Exonuclease), probe with J85324 (J85325), and then cut with SpeI (XbaI) to release part from probe. Before using the chewed end of the part, a repair step is needed (for example, fill-in with a polymerase).

Conversion of Standard Part to Self-Assembling Part

The following steps, detailed below, were used to convert BioBrick RFC10 parts to assemblable parts.
1. Start with DNA, using 100 ng to several ug of DNA from miniprep elution, and measure concentration.
2. Simultaneously digest part with XbaI and ligate to bead containing prefix overhang 1 or 2. Beaded-overhang is created by annealing anchor probe to complementary overhang and incubating with beads.
3. Wash two times in low salt buffer, last time in T4 DNA ligase buffer.
4. Cut with SpeI and PstI and wash in low salt buffer to remove backbone.
5. Elute at 80° C. in T4 buffer.
6. Simultaneously digest with SpeI and ligate to bead containing suffix overhang 2 or 1.
7. Wash.
8. Elute.
9. ExoI digest or probe with anchor complementary to prefix 1 or 2 (J8331 or J85335).

FIGS. 17, 18, 19 further illustrate these steps graphically, with boxes representing DNA.

Annealing and Self-Assembly of Assemblable Parts.

Annealing is performed by combining parts in equimolar ratios and heating to 70° C. or higher and allowing to cool to 23° C. slowly on the bench (typically 30-60 minutes).

Annealing Anchor Probe and Complementary Overhang.

Oligos were ordered from IDTDNA and resuspended at 100 uM concentration in sterile de-ionized water. Each anchor/overhang complement was combined in equal molar ratios and heated to 95° C. for 2 minutes and then allowed to cool to room temperature slowly by turning off the heat block.

Incubation of Anchor with Streptavidin Coated Beads.

40 ul of streptavidin Magnetic Beads (NEB S1420S) were washed three times in high salt binding buffer and then incubated with 20 ul of 1 uM anchor/overhang DNA for 10 minutes at room temperature. After incubation, an additional three wash steps were performed. Beads were washed by mixing, applying magnet, and removing supernatant, being careful not to disturb the beads. Other solid phase separation techniques can be used; for example, non-magnetic beads or chemical attachment to glass surfaces.

Low salt binding buffer used: 0.1 M NaCl, 20 mM Tris HCl (pH 7.5), 1 mM EDTA

High salt binding buffer used: 0.5 M NaCl, 20 mM Tris HCl (pH 7.5), 1 mM EDTA

Simultaneous Ligation with T4 DNA Ligase and Digestion with One or More BioBrick Enzymes.

BioBrick enzymes (EcoRI, XbaI, SpeI, PstI) are all active in T4 DNA ligase buffer although at somewhat reduced rates. Simultaneous ligation/digestion reactions were performed either at room temperature in T4 DNA ligase buffer supplemented with 5% PEG or in cycling reactions between low temperature ligation (16° C.) and 37° C. digestion. A final digestion step at 37° C. can be included to favor an outcome in which no unwanted ligations have occurred. Ligation times ranging from 20 minutes to several hours to overnight were used, depending on the amount of DNA to ligate and the timing constraints of the experimental procedures. Some enzymes are not suitable for extended digestion (SpeI) and will not remain active as long as the ligase. In these cases, additional amounts of enzyme were added at 37° C. for 30 minutes as a final step.

Wash Steps.

Wash steps were performed at room or slightly warmer temperatures, 37° C. being most convenient. Warm washes should not approach the melting temperature (Tm) of any annealed regions during probing. Washes may be performed in low or high salt buffer. Final washes were typically performed in T4 DNA ligase buffer before subsequent ligation or digestions reactions.

Elution.

Elution temperature must exceed the melting temperature of the annealed overhang to be eluted. For the sequences J85330-J8370, an elution temperature of 80° C. worked well. Elution temperature for other sets of sequences may differ, and can readily be calculated based on the base composition of the sequences, as will be understood by persons of skill in the art. Elution at high temperatures in water can break the biotin-streptavidin bond as well as denature DNA, so generally at least a low salt buffer was used. 1× T4 DNA ligase buffer was determined to be a generally useful elution buffer.

Probing.

A double probing is performed by first probing one overhang and then the other. When adding long overhangs, the overhang addition step can often serve as a probe step, reducing the total number of steps needed. A single probe is performed by capturing the DNA with the overhang on a complementary anchor probe already attached to a bead. The anchor probe should be single stranded. A probe is an annealing reaction that works well starting at a high temperature. To avoid disturbing the streptavidin-biotin bond, probe starting temperatures of 80° C. and in 5% PEG buffers worked well.

Removing Backbone.

When a part is attached to a bead, the backbone can be removed by cutting with XbaI or SpeI for BioBrick RFC10 parts. In some cases, EcoRI or PstI must also be used since the backbone can also ligate to the bead anchors due to the palindromic nature of the BioBrick enzymes. Later probing steps are used to eliminate any construction error this could cause.

Exo I Step.

An Exo I (NEB M0293) digestion in ExoI buffer was used to remove any single stranded DNA (ssDNA) that results from elution of unligated overhangs. This step can either save a probe step that accomplishes the same purpose, or can be used in combination with probe steps to further eliminate unwanted ssDNA. Lambda exonuclease can also be used for the same purpose if overhangs are ligated to 3' instead of 5'.

T4 Chewback.

We used a simple T4 DNA polymerase chewback reaction of 180 ng/Unit-minute of DNA for 20 minutes at 23° C. in T4 DNA ligase buffer. After 20 minutes, the enzyme was heat inactivated at 80° C.

T5 Chewback.

We used a simple T5 exonuclease chewback reaction of 20 minutes at 37° C. with a dilution of between 1:20 and 1:100 depending on DNA concentrations (empirically determined). After 20 minutes, the enzyme is heat inactivated at 80° C.

Fill In.

Fill-in reactions were performed with T4 DNA polymerase and appropriate dNTPs. NEB PreCR repair mix (M0309) also can be used.

Robotic Assembly.

Programs for digestion, ligation, bead-based DNA purification, sequence-specific purification, and annealing reactions assembly reactions along with standard screening protocols for transformation, colony picking, and restriction mapping were developed for a Tecan Evo 150 liquid handler configured with an 8-tip LiHa (liquid handling) arm and a RoMa (robotic manipulator) arm. Devices on the robot deck included a Tecan 37° C. incubator, a Torrey Pines ICXT20 (−20° C. to 100° C.) Peltier heater/chiller, an Avision AVA6 passport scanner for colony picking, an EmbiTec RunOne electrophoresis station with an EmbiTec PI-1000 PrepOne Sapphire blue illuminator, and various microplate positions, hotels and tip holders. In addition, a Tecan Safire2 plate reader was used as a shaking incubator and can measure cell optical density (OD) and DNA concentration as needed by a protocol.

Computer code written in Python (the MIT BioCAD package) was developed and used to compile scripts for robotic assembly and screening of assembly reactions. Input to robotic assembly includes an ordered-list of the names of promoters, genes, and other DNA elements to be assembled. The BioCAD package includes a database to map these names to location on deck or can be in automated storage associated with the robotic system (for example using 2D-barcoded tubes). Input can be directly from a user or generated from other software systems and bioinformatics tools such as Geneious or a frontend biocompiler.

Results

Results are shown in the figures and described herein.

Figure 1:
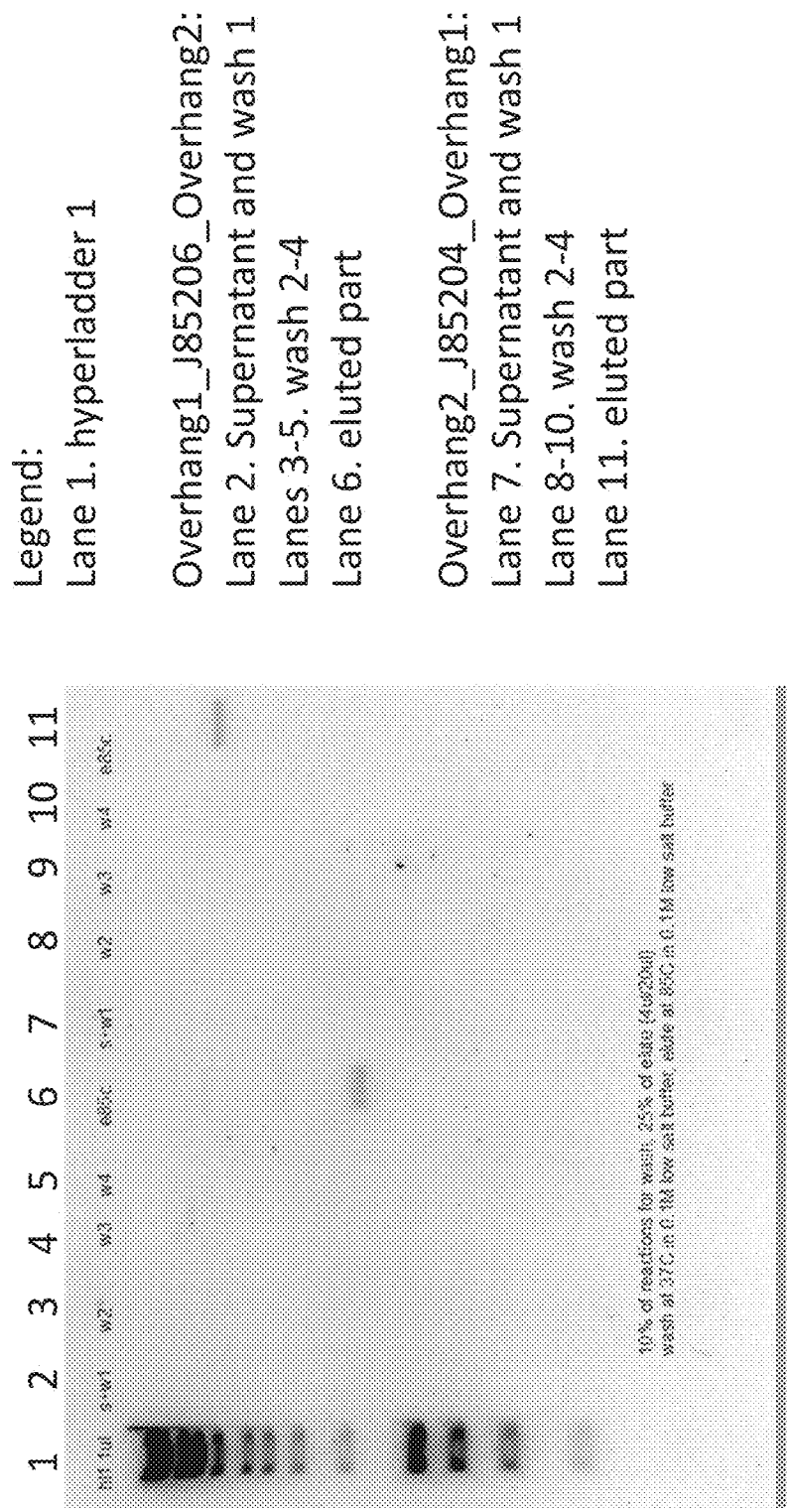
FIG. 1 shows success conversion of two RFC10 Bio-Bricks J85204 and J85206 to assemblable molecules with long overhangs. In each case, unique overhangs have been ligated to the prefix and suffix of the part. Lane 6 shows the result for J85206 and Lane 11 for J85204. The DNA is the correct length after elution, however it is otherwise not clear to see the increase in length by the small overhang.
Figure 2:
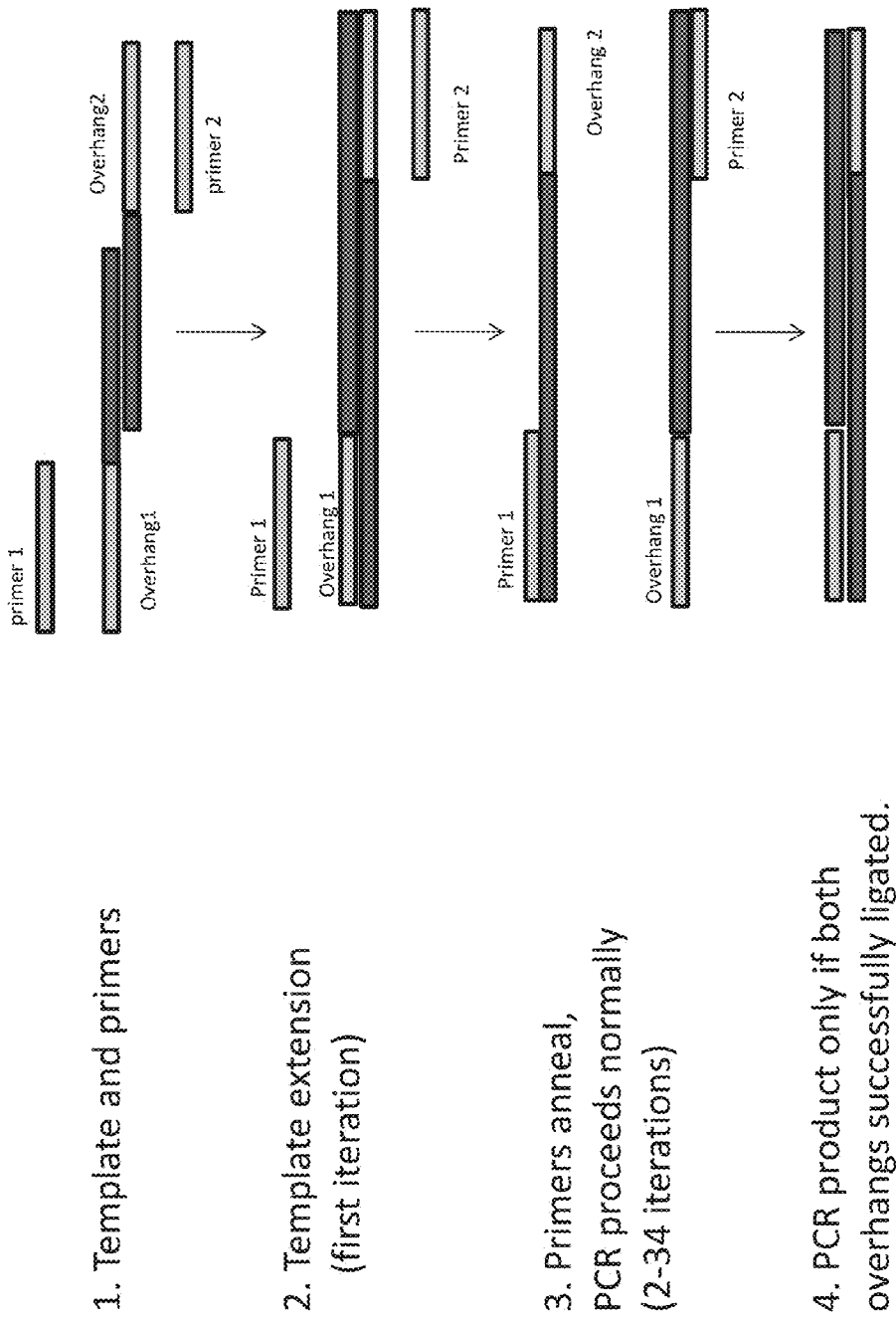

Hence FIG. 2 describes a method based on PCR to determine if any overhangs have been successfully added. Primers 1 and 2 are added to the molecule, which now serves as the template (1). Although the primers will not initially bind to the overhang since they are the same as the overhang, after a single round of extension using polymerase (2), subsequent amplification will occur (3). If amplification occurs, then at least some molecules have overhangs ligated to both ends (4).

Figure 3:
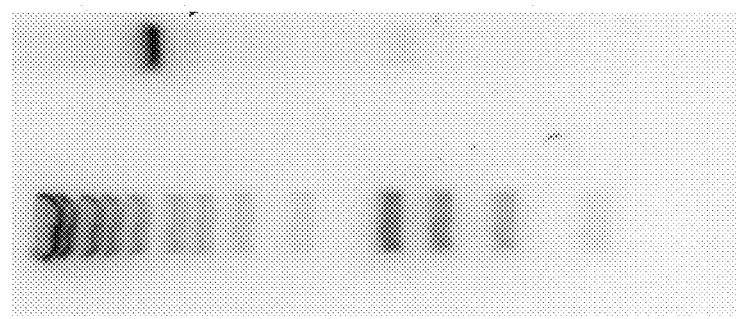

FIG. 3 shows the application of this PCR-based method to demonstrate that J85204 has been correctly converted to overhang2_J85204_overhang1. RT-PCR could additionally be used to determine the percentage of correct molecules. Note that overhang2 as prefix is part J85334 and overhang1 as a suffix is part J85333.

Figure 4:
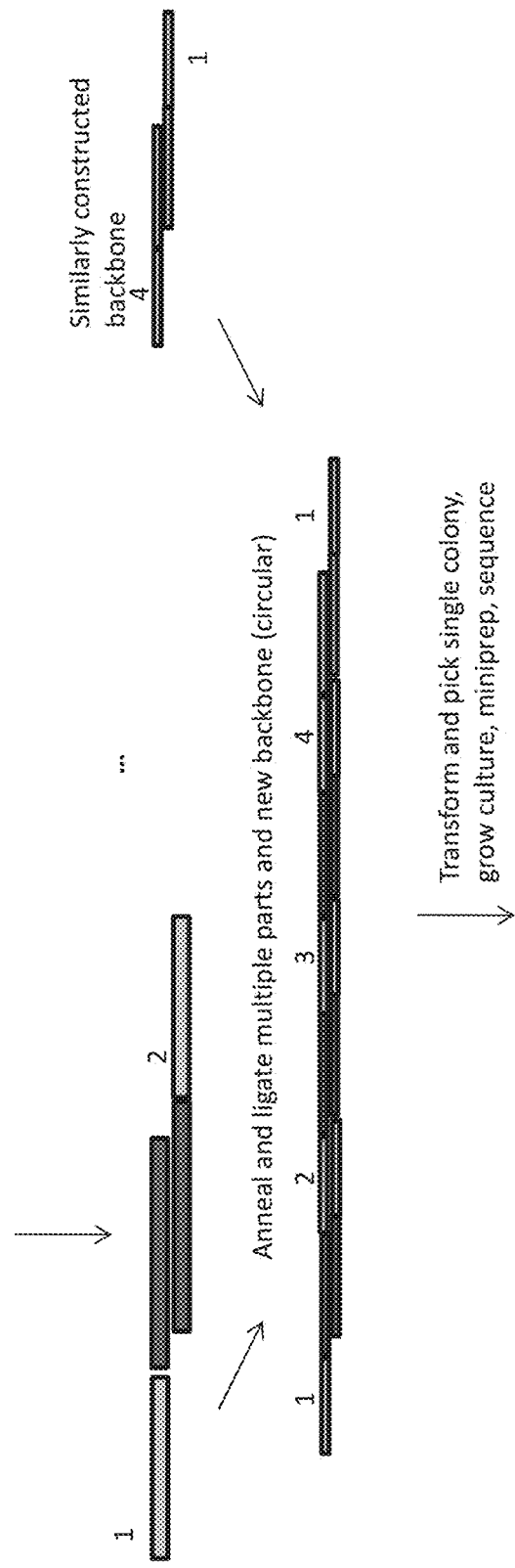

FIG. 4 shows that self-assembly is a multiway anneal requiring annealing of long overhangs. Molecules will self assemble if overhangs are complementary.

Figure 5:
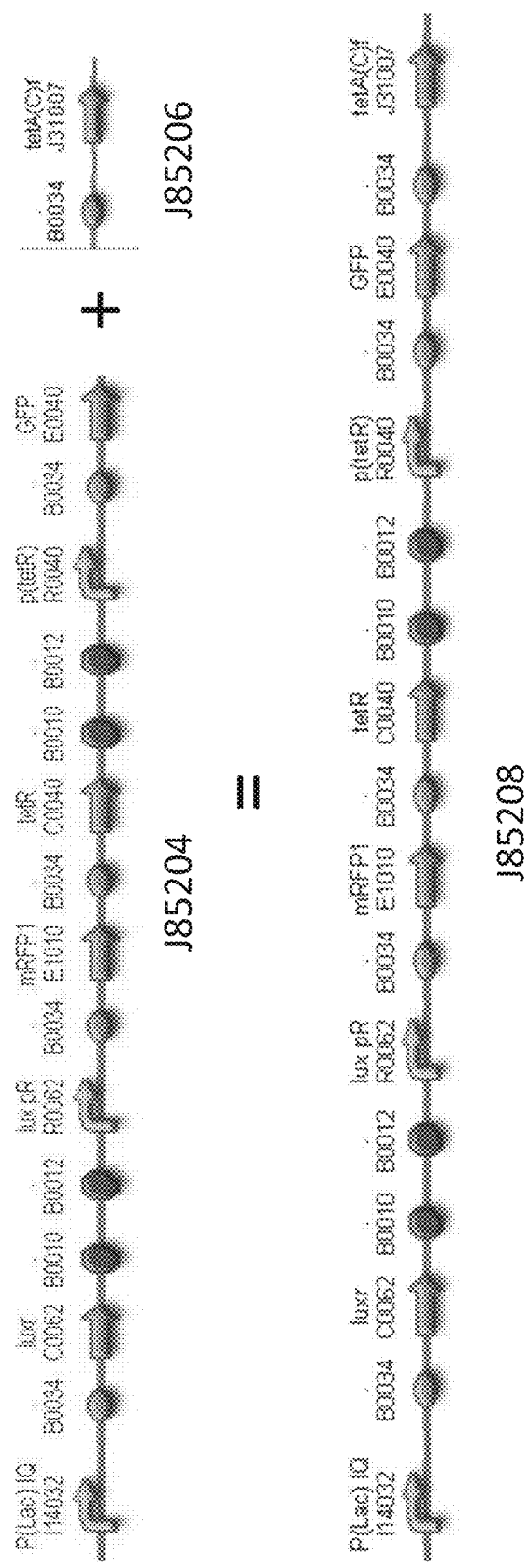

FIG. 5 shows a test case for overhang annealing. Parts J85204 and J85206 can be annealed to form part J85208.

FIG. 6 shows the result of annealing parts J85204 and J85206 to form part J85208, with a correct annealed product in lane 2, demonstrating successful self-assembly of converted parts.

Figure 7:
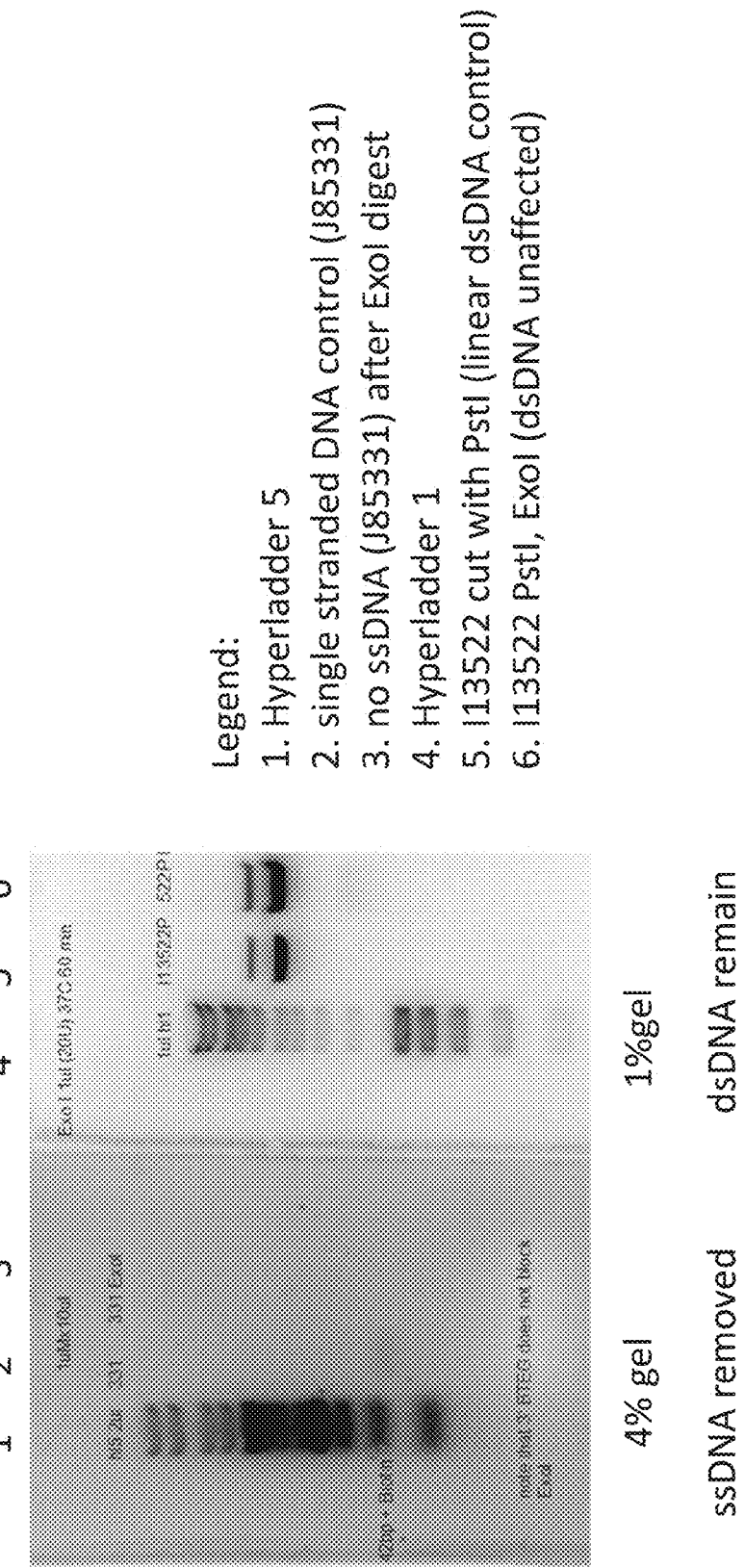

FIG. 7 shows results demonstrating that Exo I can be used to cleanup single stranded DNA without affecting double stranded DNA. I13522 is a standard BioBrick.

Figure 8:
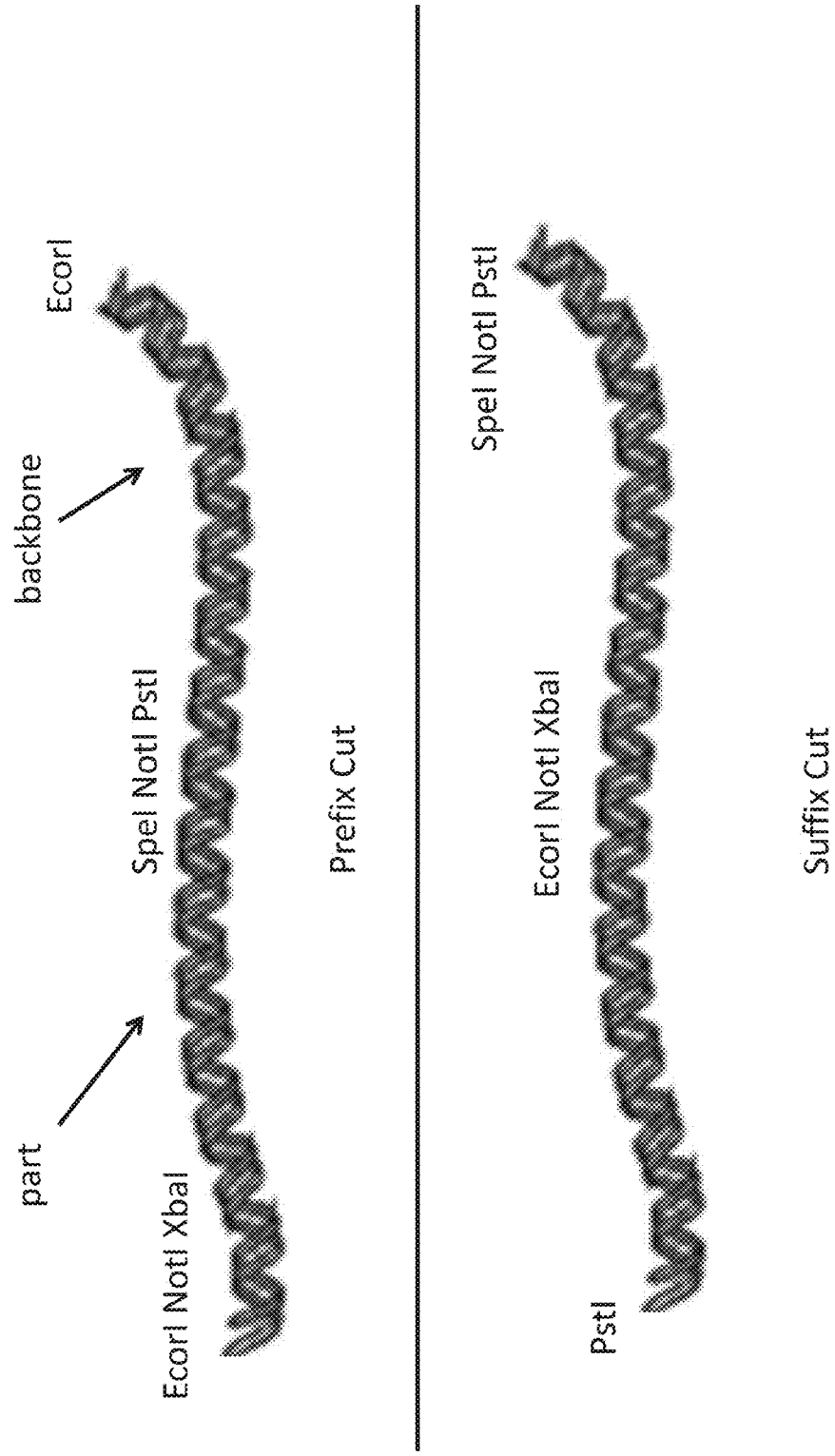

FIG. 8 shows plasmids being cut open with EcoRI or PstI in preparation for creation of temporary overhangs.

Figure 9:
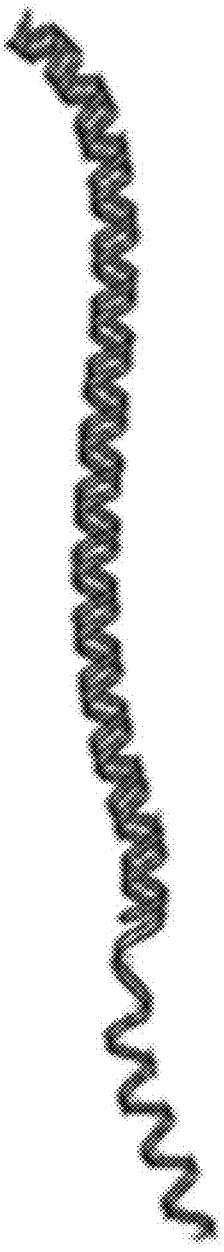

FIG. 9 shows one end of a double-stranded DNA molecule after chewback of single stranded DNA.

FIG. 10 shows probing an overhang (which may be temporary).

FIG. 11 shows the resulting sequence and complementary regions when the prefix of an RFC10 part is annealed to an anchor probe. Part (1) shows the prefix with temporary overhang annealed to an anchor probe. AATTCGCGGC-CGCTTCTAGANNNNNNNNNNNN is SEQ ID NO:1; CAAAGAAUCTTAAGCGCCGGCGAAGATCT is SEQ ID NO:2. Part (2) shows the part ligated to the anchor. AATTCGCGGCCGCTTCTAGANNNNNNNNNNNN is SEQ ID NO:3; CAAAGAAUCTTAAGCGCCGGC-GAAGATCTNNNNNNNNNNNN is SEQ ID NO:4. Part (3) shows the intersection after a fill-in reaction and with the backbone removed via an SpeI cut. AATTCGCGGCCGCT-TCTAGANNNNNNNN is SEQ ID NO:5; CAAAGAAUCTTAAGCGCCGGC-GAAGATCTNNNNNNNNNGATC is SEQ ID NO:6.

FIG. 12 illustrates backbone removal by enzyme digestion.

Figure 13:
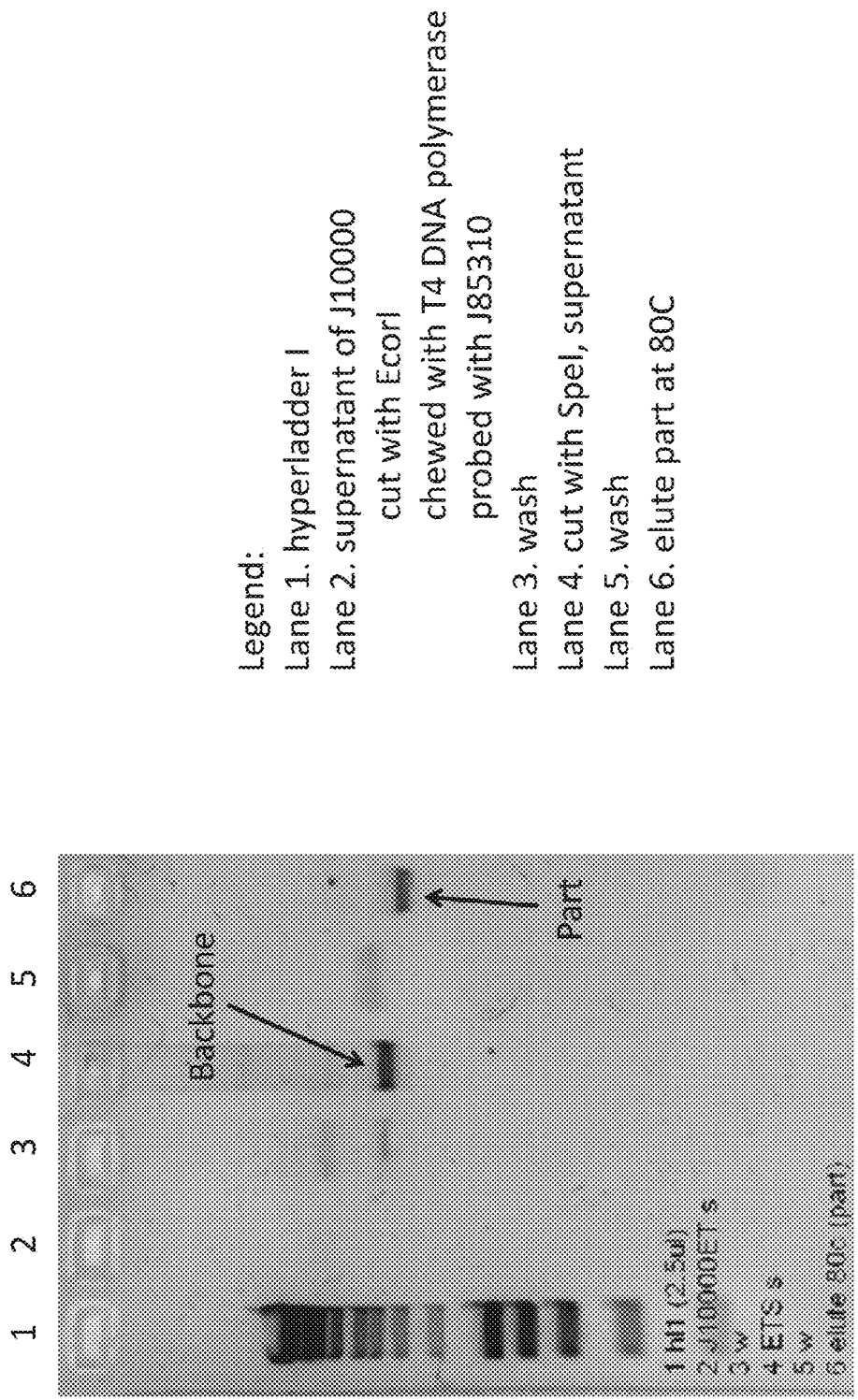

FIG. 13 shows the results generated when applying the techniques illustrated in FIG. 8-12. A BioBrick backbone was successfully separated from its part without gel extraction. A BioBrick prefix anchor was used to separate a backbone from the part (J10000 in this result) without gel extraction.

Any standard part can be captured and purified in this manner with universal prefix/suffix overhangs. The steps for this exemplary procedure were as follows:
1. Wash fresh beads
2. Incubate anchor on bead
3. Cut part with EcoRI
4. Anneal part to bead, wash
5. Cut off backbone with XbaI, wash
6. Elute purified part at 80° C.
7. After elution, other parts can be joined without an intermediate cloning step.

Figure 14:
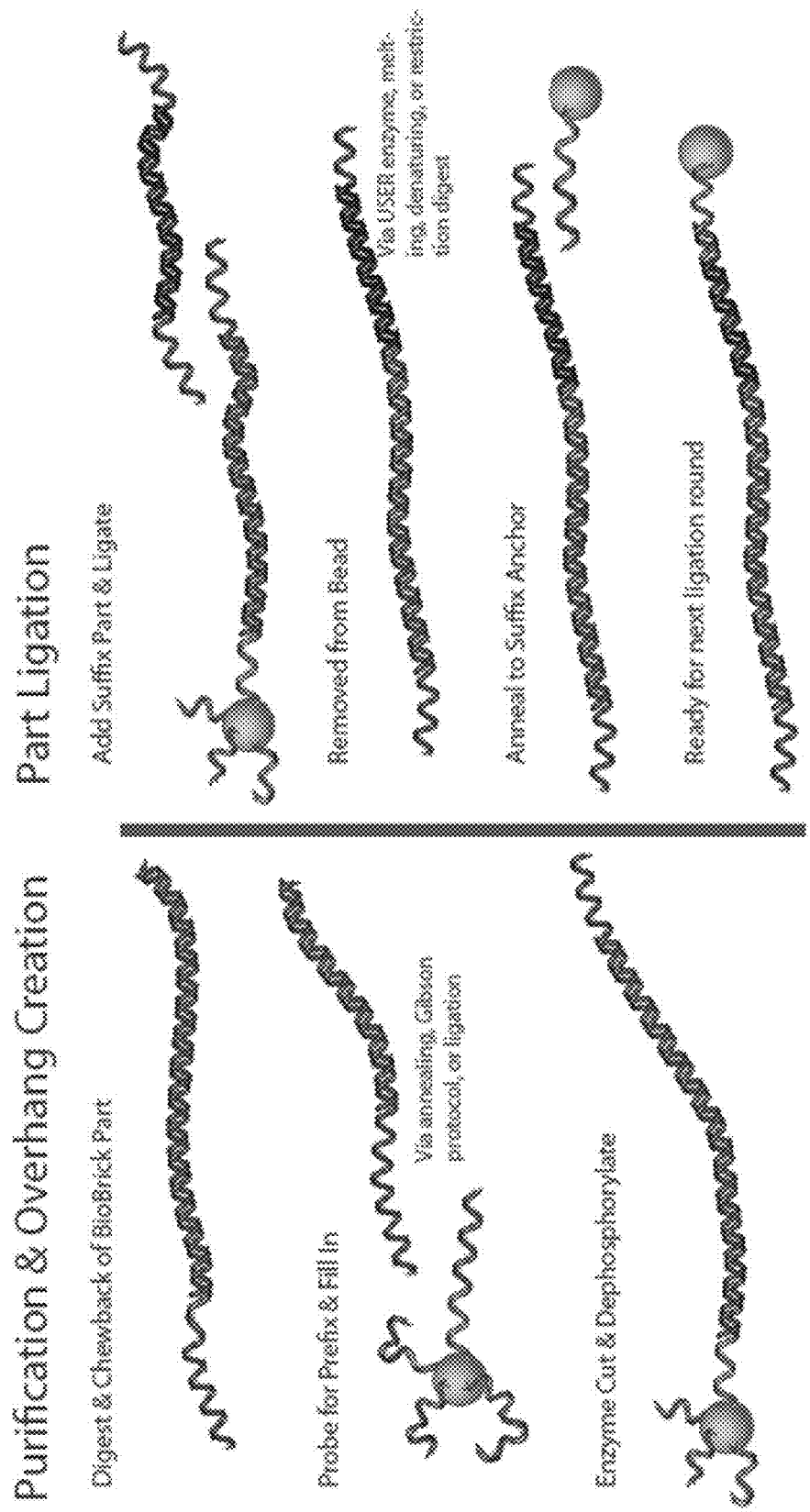
Figure 15:
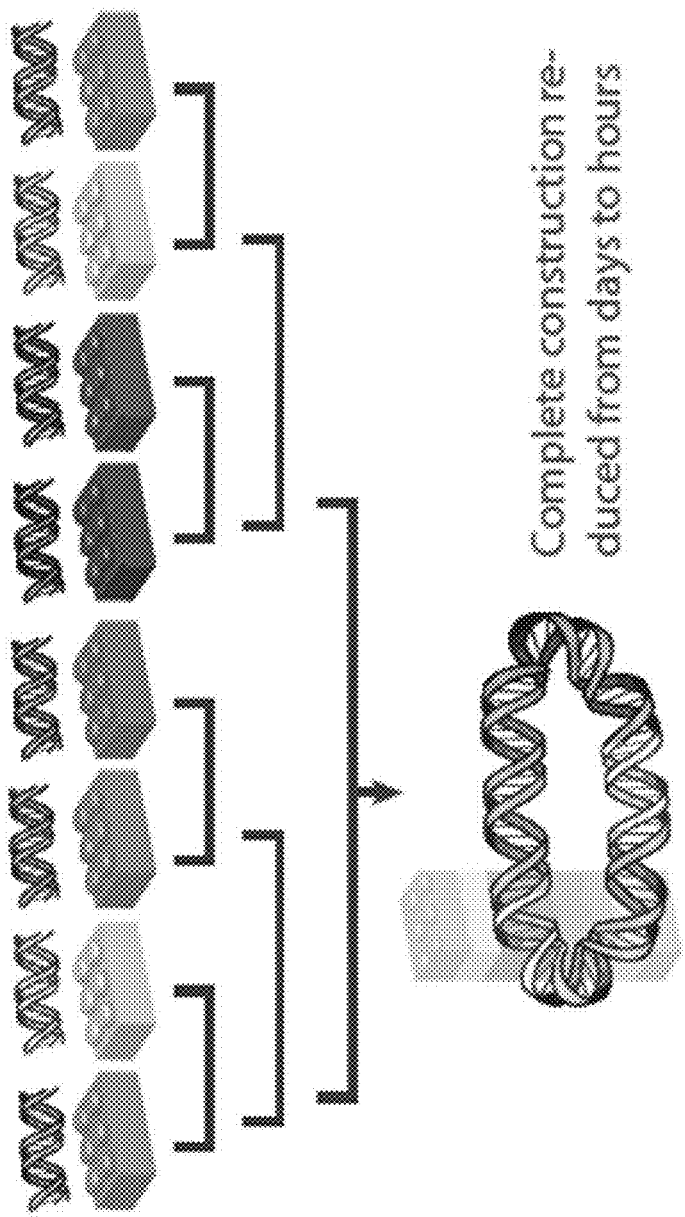

FIG. 14 further illustrates how the series of steps in FIG. 13 can be generalized to complete multistep assembly reactions without intermediate cloning steps, which can also be executed in a binary fashion (FIG. 15) in log N steps. Note that conversion of even a single part to an assemblable part as described herein requires at least a two-step reaction for RFC10 BioBricks (one step to ligate each overhang).

FIG. 16 shows the results of using an alternative procedure to FIG. 13, in which the temporary overhang is created on the backbone rather than the part with J85325. In this alternative embodiment, the part is removed from the backbone in fewer steps since the part is not directly attached to the bead and hence can be cut and taken out with the supernatant without requiring a high temperature elution step.

FIG. 17 schematically shows adding a suffix sequence to a part.

Figure 18:
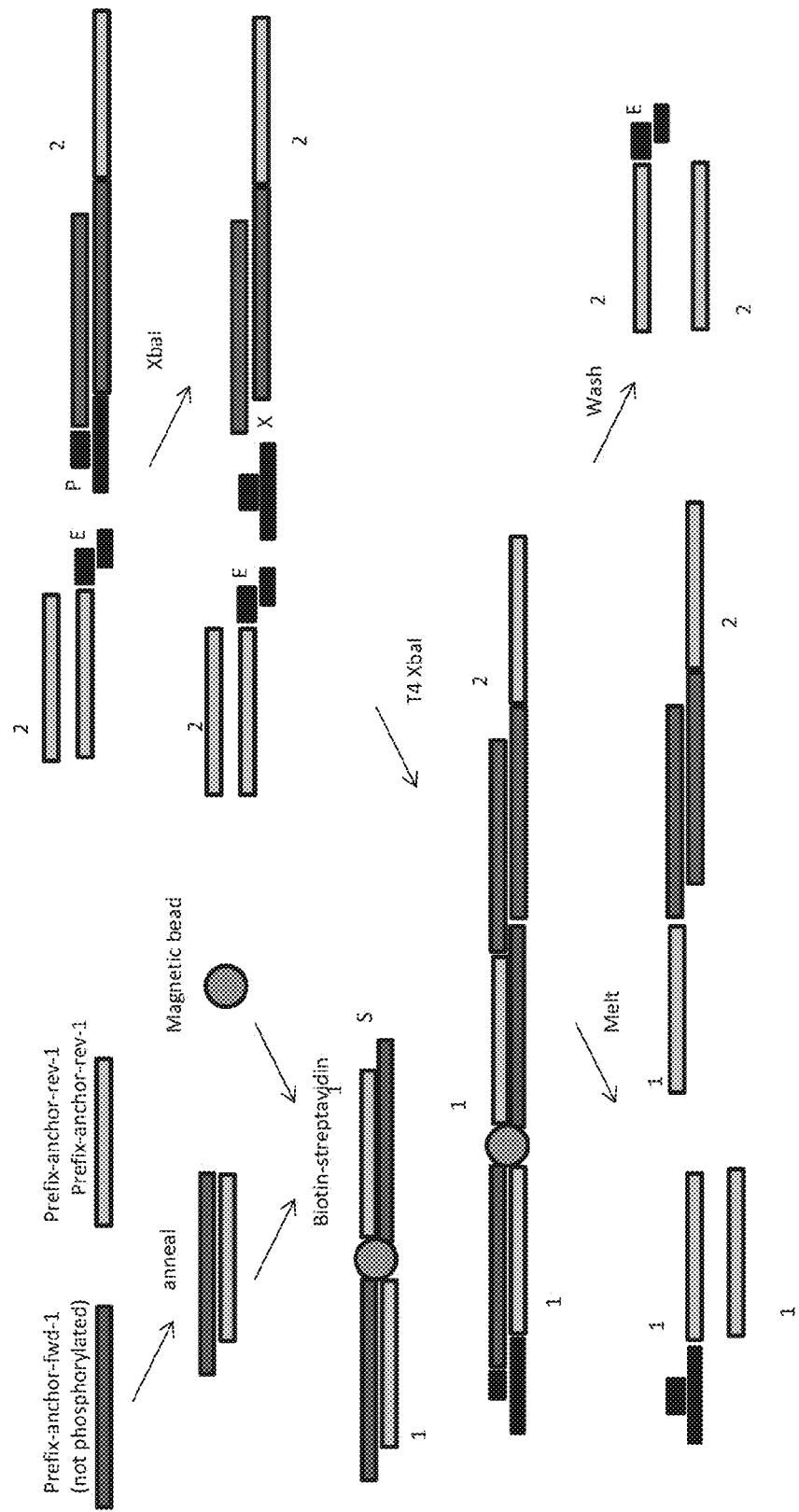

FIG. 18 schematically shows adding a prefix sequence to a part and purifying away suffix sequence after removing by digestion.

Figure 19:
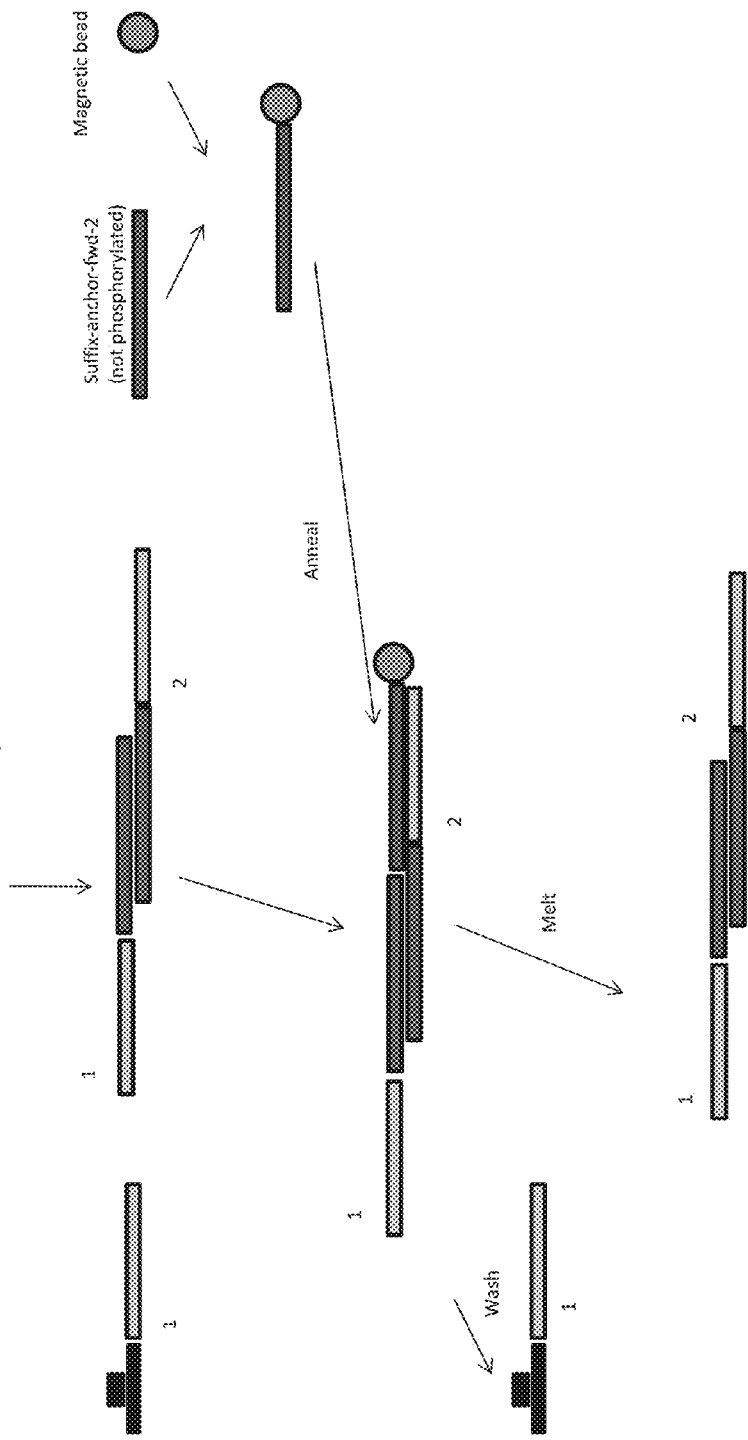

FIG. 19 schematically shows purifying away prefix sequence using a suffix anchor sequence attached to a bead.

Figure 20:
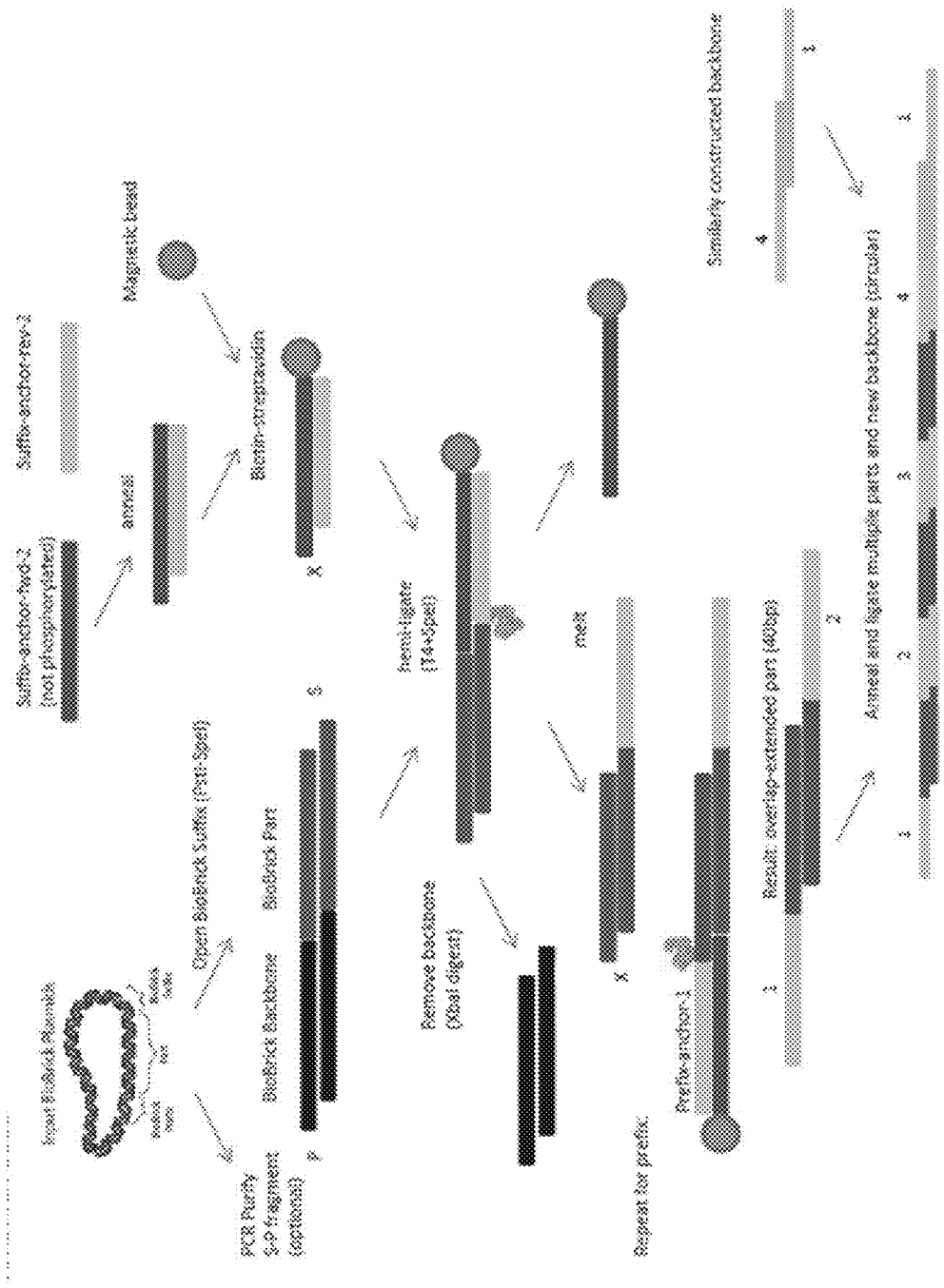

FIG. 20 shows an alternative embodiment for the method of conversion of standard parts to self-assembling parts.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Each of the foregoing patents, patent applications and references is hereby incorporated by reference, particularly for the teaching referenced herein.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of preparing a double-stranded (ds)DNA molecule, comprising:
   (a) providing a first and a second circular DNA vector, each comprising a vector backbone VB and a polynucleotide P-X-S, wherein P is a prefix nucleic acid sequence comprising an enzyme recognition site and S is a suffix nucleic acid sequence comprising an enzyme recognition site, and X is a DNA part of interest;
   (b) linearizing the first and second circular DNA vectors with an enzyme that cleaves the enzyme recognition site in the suffix of the first circular DNA vector and cleaves the enzyme recognition site in the prefix of the second circular DNA vector to produce a first and a second linear double-stranded (ds) DNA, each having a 5' overhang at each end of the linear dsDNA;
   (c) ligating the 5' overhang of the suffix of the first linear dsDNA to the 5' overhang of the prefix of the second linear dsDNA;
   (d) removing the vector backbones from the linear dsDNAs with one or more enzyme(s) that cleave(s) the enzyme recognition site in the prefix of the first linear dsDNA and in enzyme recognition site in the suffix of the second linear dsDNA to produce a single linear dsDNA comprising a prefix having a 5' overhang and a suffix having a 5' overhang; and
   (e) ligating to the 5' overhang of the prefix of the single linear dsDNA of (d) a first oligonucleotide having a length of at least 20 nucleotides and ligating to the 5' overhang of the suffix of the single linear dsDNA of (d) a second oligonucleotide having a length of at least 20 nucleotides, thereby preparing a dsDNA molecule having a 5' overhang of at least 20 nucleotides at each end of the dsDNA.

2. The method of claim 1, wherein the DNA part X of the first and/or second circular DNA vector is selected from the group consisting of: a terminator sequence, a ribosome binding site sequence, a protein coding sequence, a reporter sequence, a signaling sequence, a primer sequence, and a regulatory sequence.

3. The method of claim 1, further comprising probing the prefix and/or the suffix of the newly prepared dsDNA molecule to select a correctly prepared dsDNA molecule.

4. The method of claim 1, further comprising probing the prefix, then probing the suffix of the newly prepared dsDNA molecule to confirm the structure of the prepared dsDNA molecule.

5. The method of claim 1, wherein the first and/or second circular DNA vector comprises an origin of replication and/or an antibiotic resistance selection marker.

6. The method of claim 1, wherein the enzyme recognition sites of (a), (b) and/or (d) are Type II enzyme recognition sites.

7. The method of claim 6, wherein the Type II enzyme recognition sites are selected from EcoRI, EcoRII, BamHI, HindIII, TaqI, NotI, HinfI, Sau3, APovII, SmaI, HaeIII, HgaI, AluI, EcoRV, EcoP15I, KpnI, PstI, SacI, SalI, ScaI, SpeI, SphI, StuI and XbaI recognition sites.

8. The method of claim 1, wherein the enzyme recognition sites of (a), (b) and/or (d) are Type IIS enzyme recognition sites.

9. The method of claim 1, wherein the enzyme recognition sites of (a), (b) and/or (d) are homing enzyme recognition sites.

10. The method of claim 9, wherein the homing enzyme recognition sites are selected from I-AniI, I-CeuI, I-ChuI, I-CpaI, I-CpaII, I-CreI, I-DmoI, H-DreI, I-HmuI, I-HmuII, I-LlaI, I-MsoI, PI-PfuI, PI-PkoII, I-PorI, I-PpoI, PI-PspI, I-ScaI, I-SceI, PI-SceI, I-SceII, I-SecIII, I-SceIV, I-SceV, I-SceVI, I-SceVI, I-SceVII, I-Ssp6803I, I-TevI, I-TevII, I-TevIII, PI-TliI, PI-TliII, I-Tsp061I, I-Vdi141I, PI-PspI or PI-IsceI recognition site.

11. The method of claim 1, further comprising attaching the prepared dsDNA to a solid phase.

12. The method of claim 11, wherein the solid phase is a bead or a glass surface.

13. The method of claim12, wherein the bead is a magnetic bead.

14. A method of preparing a double-stranded (ds)DNA molecule, comprising:
   (a) providing a first, second, and at least one other circular DNA vector, each comprising a vector backbone VB and a polynucleotide P-X-S, wherein P is a prefix nucleic acid sequence comprising an enzyme recognition site and S is a suffix nucleic acid sequence comprising an enzyme recognition site, and X is a DNA part of interest;
   (b) linearizing the first, second, and at least one other circular DNA vectors with (i) a first enzyme that cleaves the enzyme recognition site in the suffix of the first circular DNA vector and cleaves the enzyme recognition site in the prefix of the second circular DNA vector and (ii) a second enzyme, having a different recognition site from the first enzyme, that cleaves the enzyme recognition site in the suffix of the second circular DNA vector and cleaves the enzyme recognition site in the prefix of the at least one other circular DNA vector to produce a first, a second, and at least one other linear double-stranded (ds) DNA, each having a 5' overhang at each end of the linear dsDNA;

(c) ligating the 5' overhang of the suffix of the first linear dsDNA to the 5' overhang of the prefix of the second linear dsDNA, ligating the 5' overhang of the suffix of the second linear dsDNA to the 5' overhang of the prefix of the at least one other linear dsDNA, to form a single linear dsDNA having a prefix and a suffix;

(d) removing the vector backbones from the single linear dsDNA with one or more enzyme(s) that cleave(s) the enzyme recognition site in the prefix of the single linear dsDNA and the enzyme recognition site in the suffix of the single linear dsDNA to produce a single linear dsDNA comprising a prefix having a 5' overhang and a suffix having a 5' overhang; and (e) ligating to the 5' overhang of the prefix of the single linear dsDNA of (d) a first oligonucleotide having a length of at least 20 nucleotides and ligating to the 5' overhang of the suffix of the single linear dsDNA of (d) a second oligonucleotide having a length of at least 20 nucleotides, thereby preparing a dsDNA molecule that comprises the X of the first, the second, the at least one other circular DNA vector and a 5' overhang of at least 20 nucleotides at each end of the dsDNA.

15. The method of claim 14, wherein the DNA part X of the first, second and/or at least one other circular DNA vector is selected from the group consisting of: a terminator sequence, a ribosome binding site sequence, a protein coding sequence, a reporter sequence, a signaling sequence, a primer sequence, and a regulatory sequence.

16. The method of claim 14, further comprising probing the prefix and/or the suffix of the newly prepared dsDNA molecule to select a correctly prepared dsDNA molecule.

17. The method of claim 14, further comprising probing the prefix, then probing the suffix of the newly prepared dsDNA molecule to confirm the structure of the prepared dsDNA molecule.

18. The method of claim 14, wherein the first, second and/or at least one other circular DNA vector comprises an origin of replication and/or an antibiotic resistance selection marker.

19. The method of claim 14, wherein the enzyme recognition sites of (a), (b) and/or (d) are Type II enzyme recognition sites.

20. The method of claim 19, wherein the Type II enzyme recognition sites are selected from EcoRI, EcoRII, BamHI, HindIII, TaqI, NotI, HinfI, Sau3, APovII, SmaI, HaeIII, HgaI, AluI, EcoRV, EcoP15I, KpnI, PstI, SacI, SalI, ScaI, SpeI, SphI, StuI and XbaI recognition sites.

21. The method of claim 14, wherein the enzyme recognition sites of (a), (b) and/or (d) are Type IIS enzyme recognition sites.

22. The method of claim 14, wherein the enzyme recognition sites of (a), (b) and/or (d) are homing enzyme recognition sites.

23. The method of claim 22, wherein the homing enzyme recognition sites are selected from I-AniI, I-CeuI, I-ChuI, I-CpaI, I-CpaII, I-CreI, I-DmoI, H-DreI, I-HmuI, I-HmuII, I-LlaI, I-MsoI, PI-PfuI, PI-PkoII, I-PorI, I-PpoI, PI-PspI, I-ScaI, I-SceI, PI-SceI, I-SceII, I-SecIII, I-SceIV, I-SceV, I-SceVI, I-SceVII, I-Ssp6803I, I-TevI, I-TevII, I-TevIII, PI-TliI, PI-TliII, I-Tsp061I, I-Vdi141I, PI-PspI or PI-IsceI recognition site.

24. The method of claim 14, further comprising attaching the prepared dsDNA to a solid phase.

25. The method of claim 24, wherein the solid phase is a bead or a glass surface.

26. The method of claim 25, wherein the bead is a magnetic bead.

* * * * *

SEQUENCE LISTING

```
<160> NUMBER OF SEQ ID NOS: 50

<210> SEQ ID NO 1
<211> LENGTH: 32
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (21)..(32)
<223> OTHER INFORMATION: n is a, c, g, or t

<400> SEQUENCE: 1
aattcgcggc cgcttctaga nnnnnnnnnn nn                                      32

<210> SEQ ID NO 2
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 2
caaagaauct taagcgccgg cgaagatct                                          29

<210> SEQ ID NO 3
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(32)
<223> OTHER INFORMATION: n is a, c, g, or t

<400> SEQUENCE: 3
aattcgcggc cgcttctaga nnnnnnnnnn nn                                      32

<210> SEQ ID NO 4
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (30)..(41)
<223> OTHER INFORMATION: n is a, c, g, t or u

<400> SEQUENCE: 4
caaagaauct taagcgccgg cgaagatctn nnnnnnnnn n                             41

<210> SEQ ID NO 5
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (21)..(28)
<223> OTHER INFORMATION: n is a, c, g, t or u

<400> SEQUENCE: 5
aattcgcggc cgcttctaga nnnnnnnn                                          28

<210> SEQ ID NO 6
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (30)..(37)
<223> OTHER INFORMATION: n is a, c, g, t or u

<400> SEQUENCE: 6
caaagaauct taagcgccgg cgaagatctn nnnnnnngat c                           41

<210> SEQ ID NO 7
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 7
agttacgcta gggataacag ggtaatatag                                        30

<210> SEQ ID NO 8
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 8
cgtaactata acggtcctaa ggtagcgaa                                         29

<210> SEQ ID NO 9
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 9
caccatctac ataacacctc aattcacaca ttcatt                                 36

<210> SEQ ID NO 10
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 10
accaattctc tccaccttta tcctaccaaa attcct                                 36

<210> SEQ ID NO 11
<211> LENGTH: 36
<212> TYPE: DNA
<213> ORGANISM: Artificial Sequence
<220> FEATURE:
<223> OTHER INFORMATION: Synthetic oligonucleotide
```

<400> SEQUENCE: 11
ttccttctct tccaccaaat ttcaacacac taacat                                    36

<210> SEQ ID NO 12
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 12
tcctatctca ctaaccaaca tcatctccat acatca                                    36

<210> SEQ ID NO 13
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 13
ttcatacctc acaaaacctc ctttctcctt ctcatt                                    36

<210> SEQ ID NO 14
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 14
ctcttcacta cacaccatat tcctctccaa atacct                                    36

<210> SEQ ID NO 15
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 15
acacattttc acaccaattc cattaaccat catcaa                                    36

<210> SEQ ID NO 16
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 16
caacactttc aacactcaat acctacaact ctactc                                    36

<210> SEQ ID NO 17
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 17
tttctttcac caaaccactt tcatacaatc tcacat                                    36

<210> SEQ ID NO 18

```
<210> SEQ ID NO 18
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 18
ctagacacca tctacataac acctcaatta caccattcat ta                              42

<210> SEQ ID NO 19
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 19
ctagtaatga atggtgtaat tgaggtgtta tgtagatggt gtctag                          46

<210> SEQ ID NO 20
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 20
ctagacacca tctacataac acctcaatta caccattcat tactag                          46

<210> SEQ ID NO 21
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 21
ctagtaatga atggtgtaat tgaggtgtta tgtagatggt gt                              42

<210> SEQ ID NO 22
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 22
ctagagccaa ttctctccac ctttatccta ccaaaattcc ta                              42

<210> SEQ ID NO 23
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 23
ctagtaggaa ttttggtagg ataaaggtgg agagaattgg ctctag                          46

<210> SEQ ID NO 24
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 24
```
ctagagccaa ttctctccac ctttatccta ccaaaattcc tactag        46

<210> SEQ ID NO 25
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 25
ctagtaggaa ttttggtagg ataaaggtgg agagaattgg ct        42

<210> SEQ ID NO 26
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 26
ctagacacca tctacataac acctcaatta caccattcat ta        42

<210> SEQ ID NO 27
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 27
ctagtaatga atggtgtaat tgaggtgtta tgtagatggt gt        42

<210> SEQ ID NO 28
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 28
ctagagccaa ttctctccac ctttatccta ccaaaattcc ta        42

<210> SEQ ID NO 29
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 29
ctagtaggaa ttttggtagg ataaaggtgg agagaattgg ct        42

<210> SEQ ID NO 30
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 30
caccatctac ataacacctc aattacacca ttcatt        36

<210> SEQ ID NO 31
<211> LENGTH: 36
<212> TYPE: DNA

<213> ORGANISM: Artificial Sequence
<220> FEATURE:
<223> OTHER INFORMATION: Synthetic oligonucleotide

<400> SEQUENCE: 31
accaattctc tccacctta tcctaccaaa attcct                    36

<210> SEQ ID NO 32
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 32
aatgaatggt gtaattgagg tgttatgtag atggtg                   36

<210> SEQ ID NO 33
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 33
aggaattttg gtaggataaa ggtggagaga attggt                   36

<210> SEQ ID NO 34
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 34
caccatctac ataacacctc aattacacca ttcattataa               40

<210> SEQ ID NO 35
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 35
aatgaatggt gtaattgagg tgttatgtag atggtg                   36

<210> SEQ ID NO 36
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 36
caccatctac ataacacctc aattacacca ttcatt                   36

<210> SEQ ID NO 37
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 37
caccatctac ataacacctc aattacacca ttcattttag               40

<210> SEQ ID NO 38
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 38
accaattctc tccaccttta tcctaccaaa attcctataa         40

<210> SEQ ID NO 39
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 39
aggaattttg gtaggataaa ggtggagaga attggt         36

<210> SEQ ID NO 40
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 40
accaattctc tccaccttta tcctaccaaa attcct         36

<210> SEQ ID NO 41
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 41
aggaattttg gtaggataaa ggtggagaga attggtttag         40

<210> SEQ ID NO 42
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is deoxyuridine

<400> SEQUENCE: 42
ctagaagcgg ccgcgaattc naagaaac         28

<210> SEQ ID NO 43
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (22)..(22)
<223> OTHER INFORMATION: n is deoxyuridine

<400> SEQUENCE: 43

```
tctagaagcg gccgcgaatt cnaagaaac                              29
```

<210> SEQ ID NO 44
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (22)..(22)
<223> OTHER INFORMATION: n is deoxyuridine

<400> SEQUENCE: 44

```
tactagtagc ggccgctgca gnaagaaac                              29
```

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 45

```
gtttcttcct gcagcggccg ctac                                   24
```

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(16)
<223> OTHER INFORMATION: n is deoxyuridine

<400> SEQUENCE: 46

```
ctgcagcggc cgctantagt a                                      21
```

<210> SEQ ID NO 47
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(24)
<223> OTHER INFORMATION: n is deoxyuridine

<400> SEQUENCE: 47

```
gtttcttcct gcagcggccg ctantagta                              29
```

<210> SEQ ID NO 48
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 48

```
gtttcttcga attcgcggcc gcttctaga                              29
```

<210> SEQ ID NO 49
<211> LENGTH: 40
<212> TYPE: DNA
<213> ORGANISM: Artificial Sequence

```
<220> FEATURE:
<223> OTHER INFORMATION: Synthetic oligonucleotide

<400> SEQUENCE: 49
aaaaaatcct tagctttcgc taaggatgat ttctggaatt                           40

<210> SEQ ID NO 50
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 50
tgcaggcttc ctcgctcact gactcgctgc gctcggtcgt                           40
```